United States Patent [19]

Choay et al.

[11] Patent Number: 4,761,430

[45] Date of Patent: Aug. 2, 1988

[54] ARYLBENZENESULFONAMIDE CONTAINING PHARMACEUTICAL COMPOSITIONS

[75] Inventors: Patrick Choay, Paris; Pierre Roger, Montigny les Bretonneux; Dominique Olliero, Montpellier, all of France

[73] Assignee: Dropic, Societe civile de gestion de droits de propriete industrielle, Paris, France

[21] Appl. No.: 910,738

[22] Filed: Sep. 23, 1986

Related U.S. Application Data

[62] Division of Ser. No. 388,964, Jun. 16, 1982, Pat. No. 4,613,618.

[30] Foreign Application Priority Data

Jun. 16, 1981 [FR] France .............................. 81 11858
Jun. 16, 1981 [FR] France .............................. 81 11859

[51] Int. Cl.[4] .................... A61K 31/19; A61K 31/215
[52] U.S. Cl. .................................... 514/562; 514/538; 514/559; 514/155
[58] Field of Search .................... 260/401; 560/12, 13; 562/430; 514/538, 559, 562, 155

[56] References Cited

U.S. PATENT DOCUMENTS 4,113,463  9/1978  Oshio et al. ........................ 560/13
4,349,378  9/1982  Cliff et al. ........................ 544/147

OTHER PUBLICATIONS

Seifter et al, *Chemical Abstracts*, vol. 59, No. 10, col. 11932 a,b, (1963).

*Primary Examiner*—Robert W. Ramsuer
*Attorney, Agent, or Firm*—Foley & Lardner, Schwartz, Jeffery, Schwaab, Mack, Blumenthal & Evans

[57] ABSTRACT

The invention relates to new medicaments having lipid regulating properties and processes for their preparation.

The medicaments according to the invention contain as active principle at least one compound, (or its corresponding optical isomer) of the arylsulfonamide type corresponding to the formula:

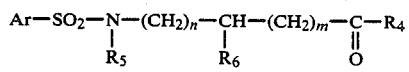

in which:
  Ar prepresents an aromatic ring which may if necessary be substituted;
  n+m+1 is comprised from 3 to 11, being preferably equal to 3, 5 or 10;
  $R_5$ and $R_6$ represent independently of one another, particularly an alkyl radical;
  $R_4$ represents the hydroxy group, the radical $OR_7$ in which $R_7$ is particularly an alkyl group, the radical $NR_8R_9$ in which $R_8$ and $R_9$ are identical or different, and represent in particular a hydrogen atom, and form with the nitrogen a nitrogenous heterocyclic ring with 5 or 6 links.

5 Claims, No Drawings

ARYLBENZENESULFONAMIDE CONTAINING PHARMACEUTICAL COMPOSITIONS

This application is a division of application Ser. No. 388,964, filed June 16, 1982, now U.S. Pat. No. 4,613,618.

The invention relates to new medicaments having lipid regulating properties and which contain, as active principle compounds having a basic structure of the arylsulfonamide type or a physiologically acceptable salt of these compounds.

The term "medicaments" will hereafter designate any pharmaceutical composition containing, in association with an acceptable pharmaceutical vehicle, one at least of the chemical compounds, such as they are hereafter defined.

The invention also relates to the process for preparing the abovesaid medicaments as well as their salts.

The medicaments according to the invention are characterized in that they correspond to the general formula:

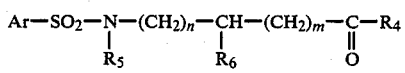  (I)

In this formula, Ar represents one of the following rings:

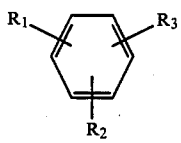

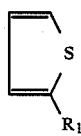

$R_1$, $R_2$, $R_3$ are identical or different and represent a hydrogen atom, a halogen atom, the $NO_2$ radical, the $NH_2$ radical, the $CF_3$ radical, an alkyl group having from 1 to 6 and preferably from 1 to 4 carbon atoms, an alkoxy group having from 1 to 6 and preferably from 1 to 4 carbon atoms, an acid group, an ester group having from 2 to 7 and preferably from 2 to 5 carbon atoms;

$n+m+1$ is comprised from 3 to 11, being preferably equal to 3, 5 or 10;

$R_5$ and $R_6$ represent, independently of one another, an hydrogen atom, an alkyl radical having from 1 to 6 carbon atoms, preferably from 1 to 4 carbon atoms, an aralkyl radical having from 7 to 9 carbon atoms;

$R_4$ represents:
  the hydroxy group,
  the group $OR_7$ in which $R_7$ is an alkyl group having from 1 to 6 carbon atoms, and preferably from 1 to 4 carbon atoms;
  the

radical in which $R_8$ and $R_9$, identical or different, represent a hydrogen atom, an alkyl group having from 1 to 6 and preferably from 1 to 4 carbon atoms, or conjointly form with nitrogen a nitrogenous heterocyclic group with 5 or 6 links, particularly a piperidino, morpholino, pyrrolidino, pyrrole or pyrroline group.

A preferred group of medicaments according to the invention is constituted by those corresponding to the general formula (I) in which $R_6$ represents a hydrogen atom. These medicaments correspond to the following general formula.

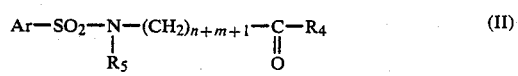  (II)

in which:

$n+m+1$ is comprised from 3 to 11, being preferably equal to 3, 5 or 10;

$R_5$ represents an alkyl radical having from 1 to 6 carbon atoms, preferably from 1 to 4 carbon atoms, an aralkyl radical having from 7 to 9 carbon atoms;

$R_4$ represents:
  the hydroxy group;
  the radical $OR_7$ in which $R_7$ is an alkyl group having from 1 to 6 carbon atoms, preferably from 1 to 4 carbon atoms;
  the radical

in which $R_8$ and $R_9$, identical or different represent a hydrogen atom, an alkyl group having from 1 to 6 and preferably from 1 to 4 carbon atoms, or conjointly form with nitrogen a nitrogenous heterocyclic radical with 5 or 6 links, particularly a piperidino, morpholino, pyrrolidino, pyrrole or pyrroline group.

In a preferred form, the medicaments according to the invention correspond to the formula (I) in which: Ar represents a substituted benzene nucleus of the formula:

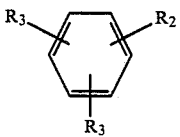

$R_1$, $R_2$ and $R_3$ having the above-indicated meanings.

In the following, $A_1$ denotes the group formed by all the medicaments of formula:

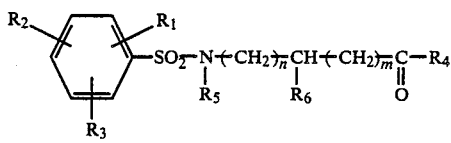

(III)

in which:

R$_1$, R$_2$, R$_3$, R$_4$, R$_5$ and R$_6$ have the above-indicated meanings;

n+m+1 is comprised from 3 to 11, being preferably equal to 3, 5 or 10.

Within this group A$_1$, a class of preferred compounds is constituted by those in which R$_6$ represents a hydrogen and corresponds to the following formula (IV):

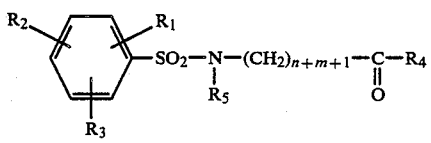

(IV)

In another preferred form, the medicaments according to the invention correspond to the formula (III) in which R$_1$, R$_2$ and R$_3$ have the above-indicated meaning and R$_5$ represents hydrogen.

These medicaments correspond to the following formula (V):

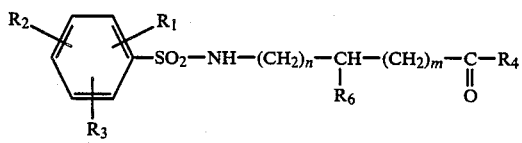

(V)

In the rest of the description, A$_2$ will denote the group formed by all medicaments of formula (V).

Within the groups A$_1$ and A$_2$, a class of preferred compounds is constituted by those of the following formula (VI):

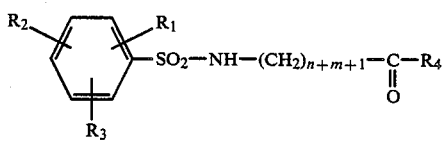

(VI)

A preferred family of medicaments according to the invention is constituted by the medicaments of formula (V) in which R$_1$, R$_2$, R$_3$ represent simultaneously a hydrogen atom, or are simultaneously different from hydrogen and are selected from the group constituted by a halogen atom, the NO$_2$ radical, the NH$_2$ radical, the CF$_3$ radical, an alkyl group having 1 to 6 and preferably from 1 to 4 carbon atoms, an alkoxy group having from 1 to 6 and preferably from 1 to 4 carbon atoms, an acid group, an ester group having from 2 to 7 and preferably from 2 to 5 carbon atoms.

The medicaments which correspond to formulae (V) and (VI) in which R$_1$, R$_2$, and R$_3$ are all three different from hydrogen form a group which will be denoted below by B$_1$.

Within this group B$_1$ an advantageous class of compounds is constituted by those in which R$_6$ represents hydrogen.

The medicaments which correspond to formula (V), in which all the substitutents of the aromatic nucleus are hydrogen, that is to say of the following formula (VII):

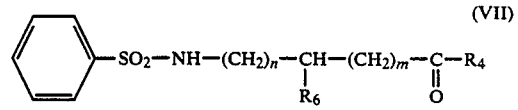

(VII)

form a group which will be denoted by B$_2$ below.

Within this group B$_2$, an advantageous class of compounds is constituted by those in which R$_6$ represents hydrogen. These compounds correspond to the following formula (VIII):

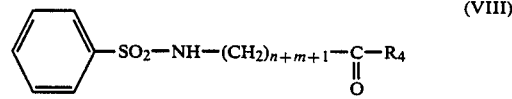

(VIII)

In the above-defined group B$_1$, a preferred class of medicaments is constituted by the medicaments of formula (V or VI) in which the benzene nucleus is trisubstituted by radicals selected from the group comprising NO$_2$, NH$_2$, OCH$_3$, CH$_3$, CF$_3$, a hydrogen atom and particularly chlorine.

This group of medicaments will be denoted by E$_1$ below.

A preferred family which corresponds to the formula (V) in which R$_1$, R$_2$ and R$_3$ are all three different from hydrogen, is constituted by that in which R$_1$, R$_2$ and R$_3$ represent simultaneously a methoxy radical.

This group will be denoted by E$_2$ in the following.

Among the medicaments of group A$_2$, a class of preferred medicaments is constituted by the medicaments corresponding to the formula (V) in which R$_1$ represents a hydrogen atom, R$_2$ and R$_3$ represents a halogen atom, the NO$_2$ radical, the NH$_2$ radical, the CF$_3$ radical, an alkyl group having from 1 to 6 and preferably from 1 to 4 carbon atoms, an alkoxy group having from 1 to 6 and preferably from 1 to 4 carbon atoms, an acid group, an ester group having from 2 to 7 and preferably from 2 to 5 carbon atoms.

These medicaments whose aromatic nucleus is disubstituted and correspond to the following formula (IX):

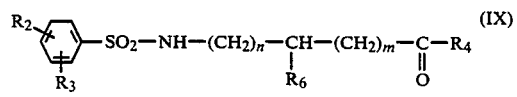

(IX)

in which R$_2$, R$_3$, R$_4$ and R$_6$ have the above-indicated meaning, form a group which will be denoted by G$_1$ in the following.

Within the above denoted group G$_1$, a preferred class of medicaments is constituted by those of the formula:

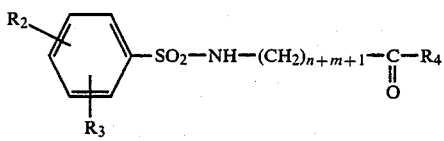

in which:

n+m+1 is comprised from 3 to 11, being preferably equal to 3, 5 or 10;

$R_2$, $R_3$ and $R_4$ having the above-indicated meaning.

Within the above-defined group $G_1$, a preferred class of medicaments is constituted by the medicaments for which the benzene nucleus is disubstituted by radicals selected from the group constituted by $NO_2$, $NH_2$, $OCH_3$, $CF_3$, $CH_3$, and by a halogen, particularly chlorine.

This group of medicaments will be denoted by $G_2$ below.

Among the medicaments of group $A_2$, a family of preferred medicaments is constituted by the medicaments corresponding to the formula (V) in which $R_1$ and $R_2$ represent simultaneously a hydrogen atom, $R_3$ representing a halogen atom, the $NO_2$ radical, $NH_2$ radical, the $CF_3$ radical, an alkyl group having from 1 to 6 and preferably from 1 to 4 carbon atoms, an alkoxy group having from 1 to 6 and preferably from 1 to 4 carbon atoms, an acid group, an ester group having from 2 to 7 and preferably from 2 to 5 carbon atoms.

These medicaments whose aromatic nucleus is monosubstituted and which correspond to the following formula (XI):

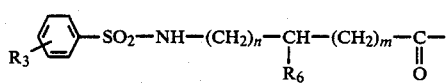

$R_3$ having the above-indicated meaning, form a group which will be denoted below by $H_1$.

Within the above-defined group $H_1$, a preferred class of compounds according to the invention is constituted by those in which $R_6$ represents a hydrogen atom. These compounds correspond to the following formula (XII):

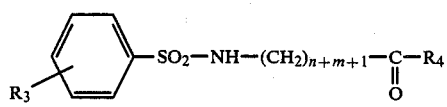

Within the above-defined group $H_1$, a preferred class of medicaments is constituted by the medicaments for which the benzene nucleus is monosubstituted by the radical selected from the group constituted by $NO_2$, $NH_2$, $CH_3$, $OCH_3$, $CF_3$, a halogen atom, and particularly chlorine.

This group of medicaments will be denoted by $H_2$ in the following.

Another family of preferred medicaments according to the invention is constituted by the medicaments of the group $A_2$ in which the benzene nucleus comprises a substituent at para position selected from the group constituted by $NO_2$, $NH_2$, $CH_3$ or $OCH_3$.

This group will be denoted in the following by K.

In another preferred embodiment of the invention, another family of preferred medicaments is constituted by the medicaments of the above-defined group $A_2$ in which the benzene nucleus comprises a substituent in the meta position selected from the group constituted by $NO_2$, $NH_2$, $CF_3$, a halogen atom, particularly chlorine.

This group of medicaments will be denoted below by L.

Within the above-defined group $A_2$, another preferred class of medicaments is constituted by those for which the benzene nucleus is substituted at the ortho position by the $OCH_3$ radical.

This group of medicaments will be denoted by M below.

In the above-defined groups $B_1$ and $E_1$, a preferred class of medicaments according to the invention is constituted by the medicaments for which the aromatic nucleus is trisubstituted:
at the para position by one of the radicals selected from the group constituted by $NO_2$ or $NH_2$;
at the meta position (that of the meta positions not included between the ortho and para substituted positions) by a halogen, particularly chlorine;
at the ortho position by the $OCH_3$ radical.

This group of medicaments will be denoted by N in the following.

Another class of preferred medicaments according to the invention is constituted by the medicaments of groups $G_1$ and $G_2$ for which the benzene nucleus is disubstituted:
at the para position by the $NH_2$ or $NO_2$ radical, a halogen atom, particularly chlorine; and
either at the meta position by the $NH_2$, $NO_2$ radical, a halogen atom, particularly chlorine;
or at the ortho position by the $OCH_3$ radical.

This group will be denoted by S in the following.

The class of medicaments belonging to the group S, disubstituted at the para position and at the meta position will be denoted by the group $S_1$ in the following.

The class of medicaments belonging to the group S, disubstituted at the para position and at the ortho position will be denoted by $S_2$ in the following.

Another class of preferred medicaments according to the invention is constituted by the medicaments of groups $H_1$ and $H_2$ for which the benzene nucleus is monosubstituted either at the para position by the radical $NO_2$, $NH_2$, $CH_3$, $OCH_3$, a halogen atom, particularly chlorine; or at the meta position by the radical $NO_2$ or by the radical $CF_3$.

This group of medicaments will be denoted by T below.

Another class of preferred medicaments according to the invention is constituted by the medicaments of formula (III):

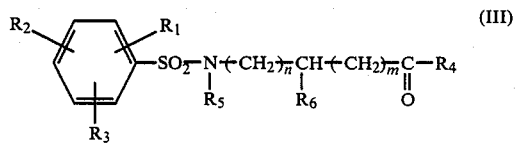

in which one at least of the substituents $R_1$, $R_2$, $R_3$ represents a $CF_3$ radical, $R_4$ represents:
the hydroxy group;
the radical $OR_7$ in which $R_7$ is an alkyl group having from 1 to 6 carbon atoms, preferably from 1 to 4 carbon atoms;

the radical

in which $R_8$ and $R_9$, identical or different, represent a hydrogen atom, an alkyl group having from 1 to 6 and preferably from 1 to 4 carbon atoms, or conjointly form with nitrogen a nitrogenous heterocyclic group with 5 or 6 links, particularly a piperidino, morpholino, pyrrolidino, pyrrole or pyrroline group;

$n+m+1$ is comprised from 3 to 11, being preferably equal to 3, 5 or 10.

This class of medicaments will be denoted by $D_1$ in the following.

Within this class $D_1$, a preferred family of medicaments according to the invention is constituted by those in which $R_6$ represents hydrogen.

Another class of preferred medicaments according to the invention is constituted by the medicaments of the formula (V):

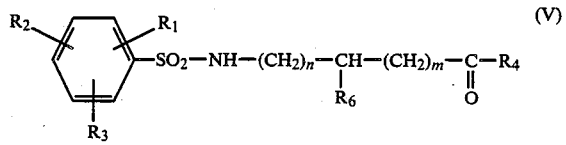

in which one at least of the substituents $R_1$, $R_2$, $R_3$ represents $CF_3$, $R_4$ represents:
the hydroxy group;
the radical $OR_7$ in which $R_7$ is an alkyl group having from 1 to 6 carbon atoms, and preferably from 1 to 4 carbon atoms;
the radical

in which $R_8$ and $R_9$, identical or different represent a hydrogen atom, an alkyl group having from 1 to 6 carbon atoms, preferably from 1 to 4 carbon atoms; or conjointly form with the nitrogen a nitrogenous heterocyclic group with 5 or 6 links, particularly a piperidino, morpholino, pyrrolidino, pyrrole or pyrroline group;

and $n+m+1$ is comprised from 3 to 11, being preferably equal to 3, 5 or 10.

This group of medicaments will be denoted by $D_2$ in the following.

Within this class $D_2$, a preferred family of medicaments according to the invention is constituted by those in which $R_6$ represents a hydrogen atom.

Another class of preferred medicaments according to the invention is constituted by the medicaments of the formula (IX):

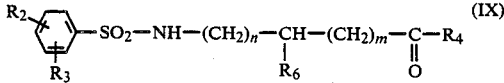

in which one at least of the substituents $R_2$ or $R_3$ represents the radical $CF_3$;

$R_4$ represents:
the hydroxy group,
the radical $OR_7$ in which $R_7$ is an alkyl group having 1 to 6 carbon atoms, preferably from 1 to 4 carbon atoms;
the radical

in which $R_8$ and $R_9$ are identical or different and represent a hydrogen atom, an alkyl group having from 1 to 6 carbon atoms, preferably from 1 to 4 carbon atoms; or conjointly form with the nitrogen a nitrogenous heterocyclic group with 5 or 6 links, particularly a piperidino, morpholino, pyrrolidino, pyrrole or pyrroline group;

and $n+m+1$ is comprised from 3 to 11, being preferably equal to 3, 5 or 10.

This class of medicaments will be denoted by $D_3$ in the following.

Within this class $D_3$, a preferred family of medicaments according to the invention, is constituted by those in which $R_6$ represents a hydrogen atom.

Another class of preferred medicaments according to the invention is constituted by medicaments of the formula (XIII):

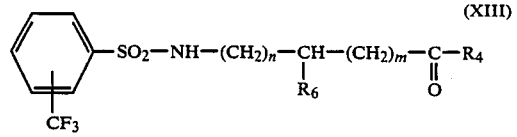

in which
$R_4$ represents:
the hydroxy group,
the radical $OR_7$ in which $R_7$ is an alkyl group having from 1 to 6 carbon atoms, preferably from 1 to 4 carbon atoms;
the radical

in which $R_8$ and $R_9$ are identical or different and represent a hydrogen atom, an alkyl group having from 1 to 6 carbon atoms and preferably from 1 to 4 carbon atoms, or conjointly form with nitrogen a heterocyclic nitrogenous group with 5 or 6 links, particularly a piperidino, morpholino, pyrrolidino, pyrrole or pyrroline group;

and $n+m+1$ is comprised from 3 to 11, being preferably equal to 3, 5 or 10.

This class of medicaments will be denoted by $D_4$ in the following.

Within this class $D_4$, a preferred family of medicaments according to the invention is constituted by those in which $R_6$ represents a hydrogen atom.

Another class of preferred medicaments according to the invention is constituted by the medicaments of the formula (XIII):

$$\text{Ar}-SO_2-NH-(CH_2)_n-\underset{R_6}{CH}-(CH_2)_m-\underset{O}{\overset{\|}{C}}-R_4 \quad \text{(XIII)}$$

(with CF$_3$ on the ring)

in which R$_4$ represents OH or C$_2$H$_5$ and n+m+1 is comprised from 3 to 11, being preferably equal to 3, 5 or 10.

This group of medicaments will be denoted by D$_5$ below.

Within this class D$_5$, a preferred family of medicaments according to the invention is constituted by those in which R$_6$ represents a hydrogen atom.

These medicaments correspond to the following formula (XIV):

$$\text{Ar}-SO_2-NH-(CH_2)_{n+m+1}-\overset{\|}{\underset{O}{C}}-R_4 \quad \text{(XIV)}$$

(with CF$_3$ on the ring)

Another class of preferred medicaments according to the invention is constituted by the medicaments of the formula (XIII):

$$\text{Ar}-SO_2-NH-(CH_2)_n-\underset{R_6}{CH}-(CH_2)_m-\overset{\|}{\underset{O}{C}}-R_4 \quad \text{(XIII)}$$

(with CF$_3$ on the ring)

in which
R$_4$ represents:
the hydroxy group,
the radical OR$_7$ in which R$_7$ is an alkyl group having from 1 to 6 carbon atoms, preferably from 1 to 4 carbon atoms;
the radical $$N\overset{-R_8}{\underset{R_9}{\diagdown}}$$

in which R$_8$ and R$_9$, identical or different, represent a hydrogen atom, an alkyl group having from 1 to 6 carbon atoms, preferably from 1 to 4 carbon atoms,
and n+m+1 equals 3, 5 or 10.

This class of medicaments will be denoted by D$_6$ in the following.

Within this class D$_6$, a preferred family of medicaments according to the invention is constituted by those in which R$_6$ represents a hydrogen atom.

Another class of preferred medicaments according to the invention is constituted by the medicaments of the following formula (XV):

$$\text{Ar}-SO_2-NH-(CH_2)_n-\underset{R_6}{CH}-(CH_2)_m-\overset{\|}{\underset{O}{C}}-R_4 \quad \text{(XV)}$$

(with CF$_3$ on the ring)

in which
R$_4$ represents:
the hydroxy group,
the radical OR$_7$ in which R$_7$ is an alkyl group having from 1 to 6 carbon atoms, and preferably the group C$_2$H$_5$,
the radical $$N\overset{-R_8}{\underset{R_9}{\diagdown}}$$

in which R$_8$ and R$_9$ are identical or different and represent a hydrogen atom, an alkyl group having from 1 to 6, preferably from 1 to 4 carbon atoms, or conjointly form with nitrogen a nitrogenous heterocyclic group with 5 or 6 links, particularly a piperidino, morpholino, pyrrolidino, pyrrole or pyrroline group;
n+m+1 is comprised from 3 to 11, and preferably takes the values of 3, 5 or 10.

This class of medicaments will be denoted below by D$_7$.

Among this class D$_7$, a preferred family of medicaments in accordance with the invention is constituted by those in which R$_6$ represents a hydrogen atom.

These medicaments correspond to the formula (XVI):

$$\text{Ar}-SO_2-NH-(CH_2)_{n+m+1}-\overset{\|}{\underset{O}{C}}-R_4 \quad \text{(XVI)}$$

(with CF$_3$ on the ring)

According to still another preferred embodiment of the invention, a preferred class of medicaments corresponds to the formula (I) in which:
Ar represents the ring of formula:

(thiophene ring with S)

this ring being possibly substituted particularly at the position of the sulfur by a halogen, particularly chlorine, or by a methyl radical.

The radical Ar is preferably attached to the chain:

$$-SO_2-\underset{R_5}{N}-(CH_2)_n-\underset{R_6}{CH}-(CH_2)_m-\overset{\|}{\underset{O}{C}}-R_4$$

through the carbon atom situated at the α position with respect to the sulfur.

This group of medicaments will be denoted by W below.

According to another embodiment, a preferred class of medicaments corresponds to the formula (I) in which:

Ar represents the ring of formula:

this ring being possibly substituted by CF$_3$, a halogen, particularly chlorine, or an alkyl group having 1 to 6 carbon atoms, particularly methyl.

In this class of medicaments, the radical Ar is preferably attached to the chain:

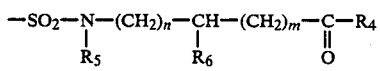

through the carbon atom situated at the meta position with respect to the nitrogen.

This group of medicaments will be denoted by X below.

Within this group X, a preferred class of medicaments is constituted by those in which R$_6$ represents a hydrogen atom.

These medicaments correspond to the formula:

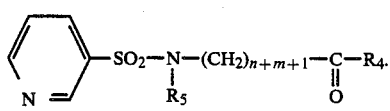

Another family of medicaments is constituted by those of the formula (III):

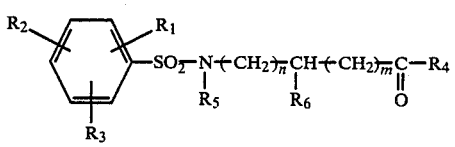

in which R$_1$, R$_2$ represent hydrogen and R$_3$ a halogen, particularly chlorine, NO$_2$ and R$_5$ represents an alkyl radical having from 1 to 6 carbon atoms, particularly the methyl radical.

This group of medicaments will be denoted below by Q.

Among this group Q, a preferred class of medicaments is constituted by those in which R$_6$ represents a hydrogen atom.

In a preferred group of medicaments according to the invention, belonging to any one of the groups A$_1$, A$_2$, W, X or Q, n advantageously takes the values 3, 5 or 10.

This group of medicaments will be denoted below by Y.

In another preferred group of medicaments according to the invention, belonging to any one of the groups A, W, X, Y or Q, R$_4$ represents advantageously the hydroxy radical or the OC$_2$H$_5$ radical.

This group of medicaments will be denoted by Z below.

The invention also relates to medicaments containing by way of active substance the optical isomers of the compounds of formula (I), as well as the physiologically acceptable salts of these optical isomers.

The particularly preferred medicaments according to the invention are those of the formula:

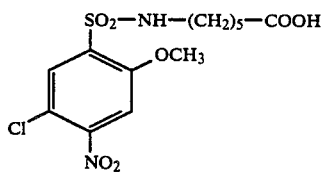

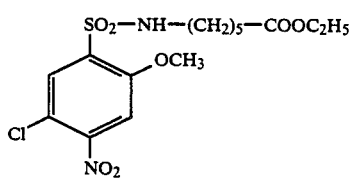

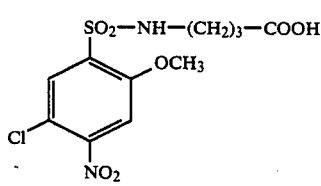

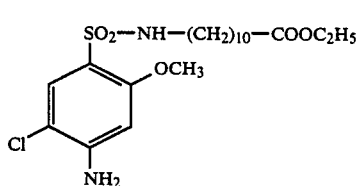

, TsOH

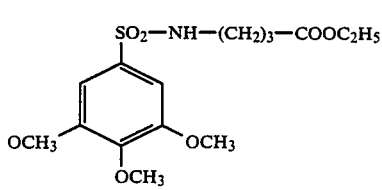

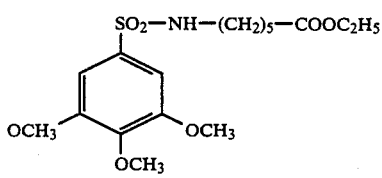

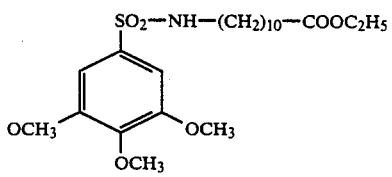

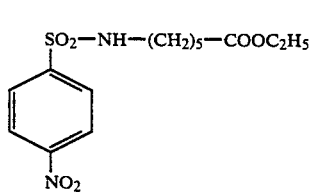

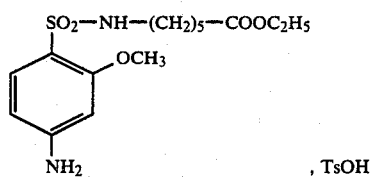
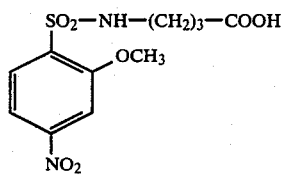
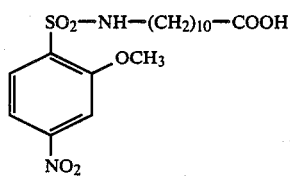
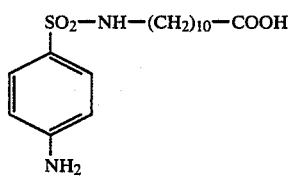
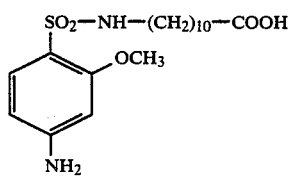
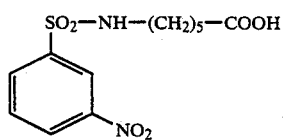
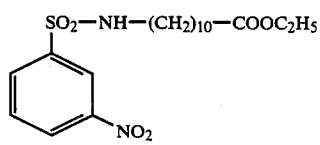
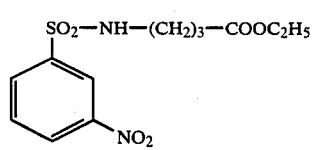
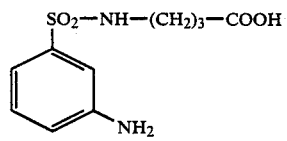
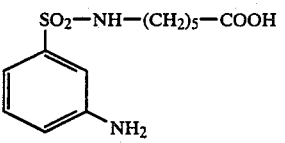
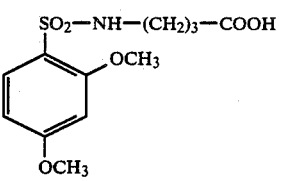
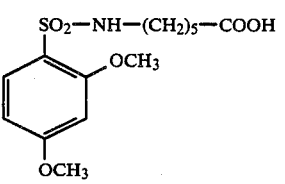
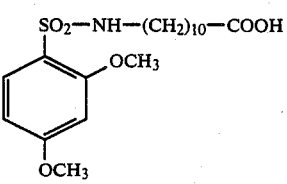
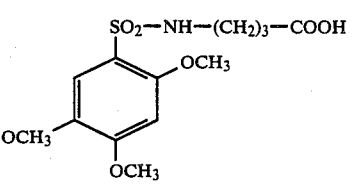
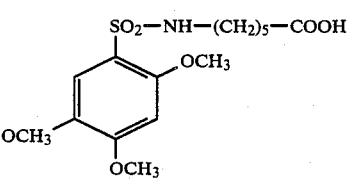
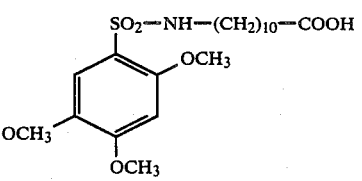
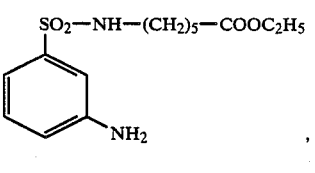
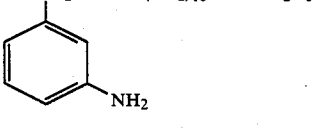

-continued
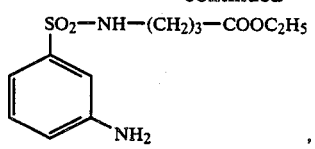
, TsOH
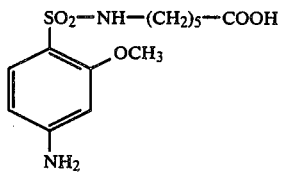
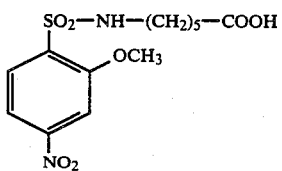
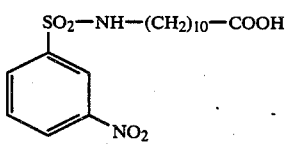
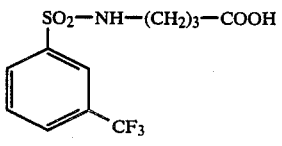
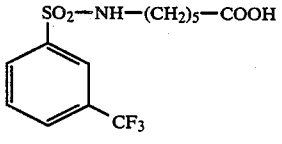
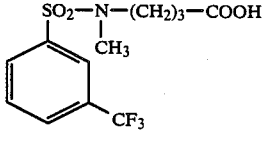
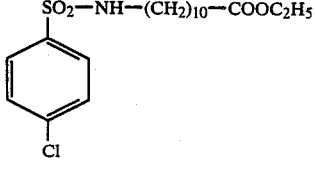
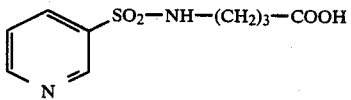
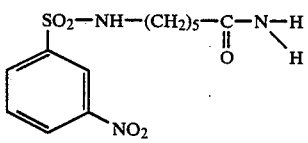
-continued
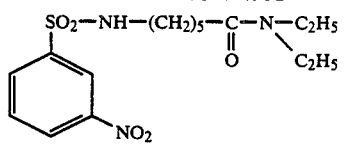
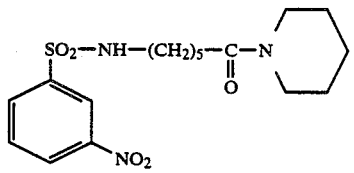
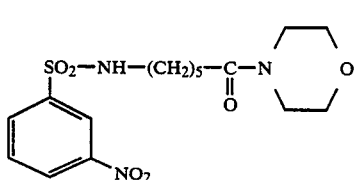
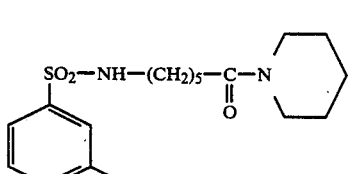
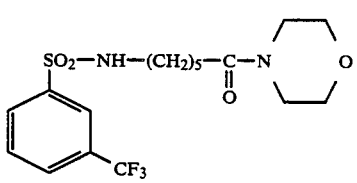
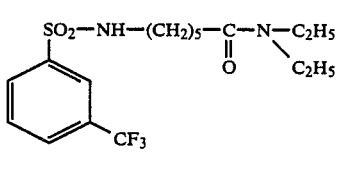
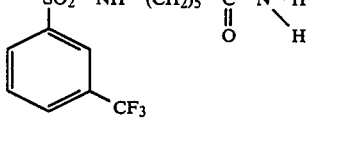
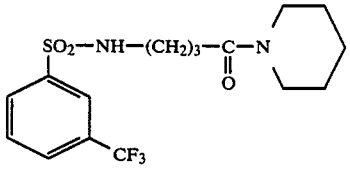
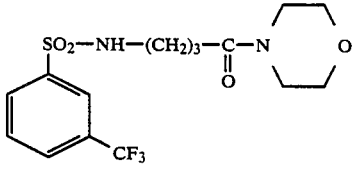

-continued

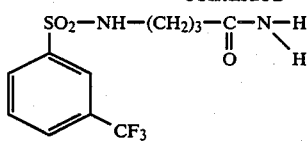

The compounds which are part of the pharmaceutical compositions (medicaments) constitute new industrial products, with the proviso that when Ar represents the benzene nucleus and when $R_4$ represents an hydroxy group or the $OR_7$ radical, one at least of the three substituents $R_1$, $R_2$ or $R_3$ represents the $CF_3$ radical.

Consequently, are part of the invention and are claimed the groups of new products corresponding to the respective groups of medicaments above mentioned with the proviso that when Ar represents the benzene nucleus and when $R_4$ represents an hydroxy group or the $OR_7$ radical, one at least of the three substituents $R_1$, $R_2$ or $R_3$, represents the $CF_3$ radical.

In other words, the new industrial products according to the invention correspond to the compounds which are part of the pharmaceutical compositions with the proviso that when Ar represents the benzene nucleus and when $R_4$ is different from

one at least of the three substituents $R_1$, $R_2$ or $R_3$ represents the $CF_3$ radical.

The classes of preferred compounds correspond to the preferred classes of medicaments above mentioned with the above said proviso.

Particularly, preferred compounds according to the invention are those of the following formulae:

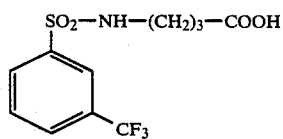

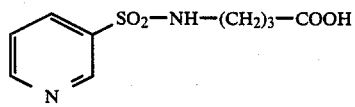

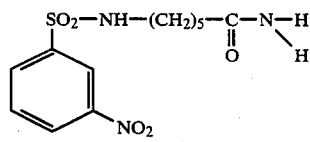

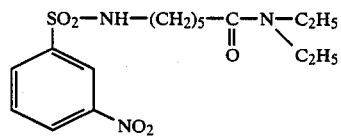

-continued

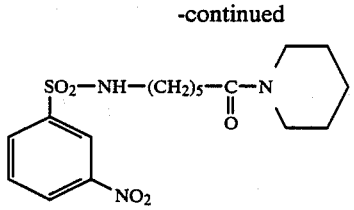

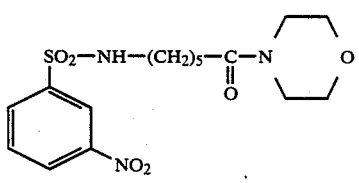

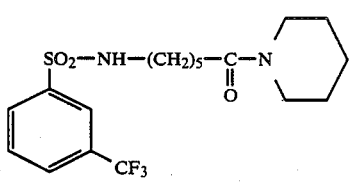

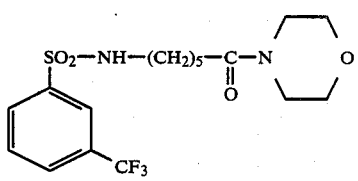

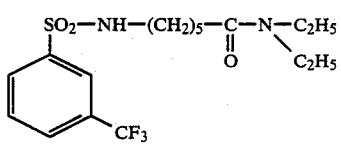

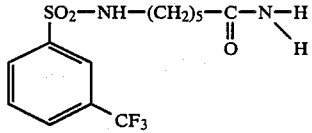

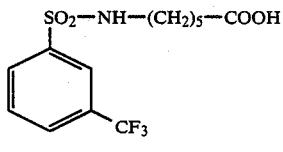

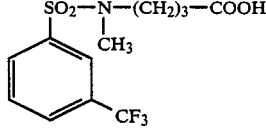

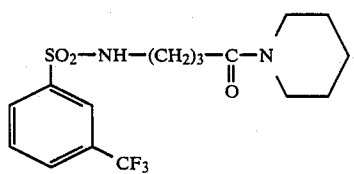

-continued

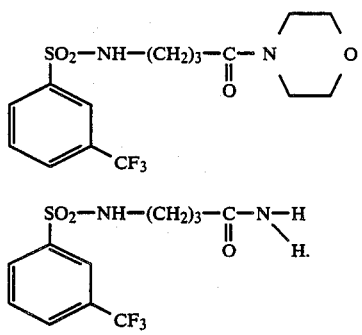

SYNTHESIS OF THE MEDICAMENTS AND NEW COMPOUNDS ACCORDING TO THE INVENTION

In the following, the syntheses of new compounds according to the invention as well as the synthesis of medicaments are described.

A first method of preparation (PROCESS IA) of the medicaments of the formula:

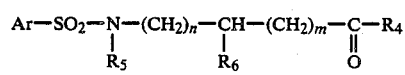

in which:
$R_4$ represents the radical $OR_7$, $R_7$ being an alkyl group having from 1 to 6 carbon atoms;
$R_5$ and $R_6$ have the above indicated meanings; and of new compounds of formula:

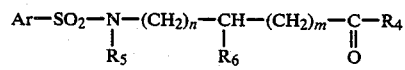

in which:
$R_4$ represents the radical $OR_7$, $R_7$ being an alkyl group having from 1 to 6 carbon atoms,
$R_5$ and $R_6$ have the above indicated meanings, with the proviso that when Ar represents the benzene nucleus, it is substituted by at least one $CF_3$ group;
consists in reacting a halide, particularly a suitable acid chloride of the formula:

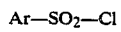

with an amino-ester of the formula:

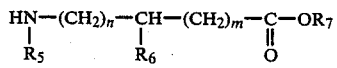

or its hydrochloride of formula:

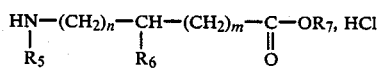

according to the following diagram:

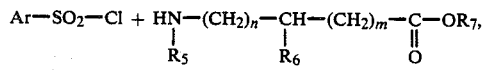

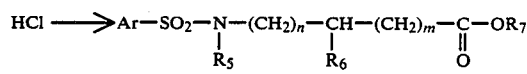

In these formulae Ar, n, m and $R_5$, $R_6$, $R_7$ have the previously indicated meanings.

From the practical point of view, procedure is advantageously as follows.

The amino-ester or its hydrochloride ($2 \times 10^{-2}$ mole) in anhydrous benzene (50 cm$^3$) is stirred vigorously at a temperature of 0° to 5° C.; triethylamine (or another organic base of the type of a tertiary amine) is then added (15 to 20 cm3), then 5 to 10 minutes later, the acid chloride ($2 \times 10^{-2}$ mole) in small amounts or drop by drop, according it is in solid or liquid form. The triethylamine is added in excess because it enables to neutralize when necessary the hydrochloride of the amino-acid in the form of its corresponding base and in any case, it enables to neutralize the hydrochlorhydric acid resulting from the reaction of condensation between Ar-SO$_2$Cl and the amino-ester. The reaction medium comes back gradually to room temperature and, after 12 hours, the crystals of triethylamine hydrochloride formed are filtered and rinsed with benzene. The organic phase is concentrated, then taken up again with ethyl acetate (200 cm3); the latter solution is washed successively with solutions of dilute hydrochloric acid and dilute sodium bicarbonate, dried and the solvent is evaporated off.

The residue so obtained is chromatographed if necessary.

In general, the acid chloride is available commercially.

When it is not available, it is possible to synthesize it by conventional methods.

For example, in the case of 2-thiophene sulfonyl chloride, procedure is as indicated by E. MACCARONE, G. MUSUMARRA and G. A. TOMASELLI, Ann. Chim. Rome, 1973, 63, 861, according to the following diagram:

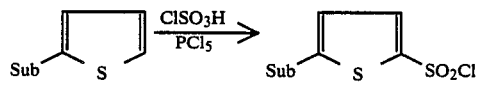

A Preferred group of thiophene sulfochlorides is constituted by those of the formula:

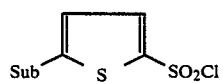

in which Sub represents a halogen atom, an alkyl group having from 1 to 3 carbon atoms and preferably 1 carbon atom, particularly chlorine or the radical $CH_3$.

In the case 3-pyridine sulfonyl chloride procedure is as indicated by M. F. ZIENTY, J. Amer. Pharm. Assoc., 1948, 37, 97 according to the diagram:

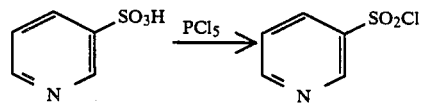

The following example illustrates the method of preparation of medicaments according to the invention, for which preparation recourse is had to the above-indicated process in its generality.

EXAMPLE I

Preparation of ethylic ester of (thiophene-2-sulfonylamino)-11 undecanoic acid

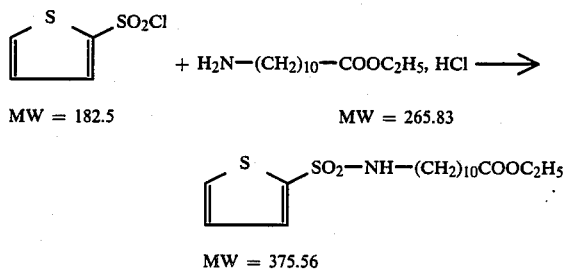

To a hydrochloride suspension of the ethyl ester of 11-amino undecanoic acid ($4.5 \times 10^{-2}$ mole = 11.96 g) in anhydrous bezene (100 cm$^3$), cooled in a water and ice bath and with magnetic stirring, is added after five minutes, triethylamine (15 cm$^3$). After ten minutes, thiophenesulfonyl chloride is added ($4.5 \times 10^{-2}$ mole = 8.6 g) in anhydrous benzene (10 cm$^3$).

After stirring overnight, at room temperature, the reaction medium was filtered (the triethylamine hydrochloride crystals were removed after having been rinsed with benzene) and the filtrate concentrated under reduced pressure. The residue was extracted with ethyl acetate (200 cm$^3$) in the presence of a 5% hydrochloride acid solution (200 cm$^3$); the organic phase was then washed successively with water, a 5% sodium carbonate solution and water, dried over sodium sulfate and concentrated under reduced pressure. The product was concentrated on silica H and the desired product, eluted with benzene/ethyl acetate mixture (9:1), was obtained pure with a yield of 91%.

The medicaments gathered in Table I below and the new products gathered in Table I below were prepared according to this process.

TABLE I

FIRST PROCESS FOR THE SYNTHESIS OF MEDICAMENTS OF FORMULA:

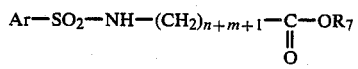

| no | Ar | n + m + 1 | R$_7$ | MP °C. | Formula/MW | Reaction yield (%) |
|---|---|---|---|---|---|---|
| 486 | 4-Cl, 2-OCH$_3$, 5-NO$_2$ phenyl | 3 | C$_2$H$_5$ | 110 | C$_{13}$H$_{17}$ClN$_2$O$_7$S = 380,80 | 65 (95) |
| 735 | " | 4 | " | 116 | C$_{14}$H$_{19}$ClN$_2$O$_7$S = 394,85 | 84 |
| 380 | " | 5 | " | 68 | C$_{15}$H$_{21}$ClN$_2$O$_7$S = 408,86 | 64 (55) |
| 508 | " | 7 | " | 70 | C$_{17}$H$_{25}$ClN$_2$O$_7$S = 436,91 | 63 |
| 502 | " | 10 | " | 83 | C$_{20}$H$_{31}$ClN$_2$O$_7$S = 478,99 | 83 (97) |
| 807 | " | 11 | " | 88 | C$_{21}$H$_{33}$ClN$_2$O$_7$S = 493,03 | 69 |
| 1 027 | 3,4,5-tri-OCH$_3$ phenyl | 3 | " | 94 | C$_{15}$H$_{23}$NO$_7$S = 361,42 | 55 |
| 865 | " | 5 | " | 120 | C$_{17}$H$_{27}$NO$_7$S = 389,48 | 40 |
| 1 028 | " | 10 | " | 77 | C$_{22}$H$_{37}$NO$_7$S = 459,61 | 40 |
| 625 | 2-OCH$_3$, 4-NO$_2$ phenyl | 3 | " | 97 | C$_{13}$H$_{18}$N$_2$O$_7$S = 346,36 | (72) |
| 608 | " | 5 | " | 88 | C$_{15}$H$_{22}$N$_2$O$_7$S = 374,41 | 86 |
| 611 | " | 10 | " | 68 | C$_{20}$H$_{32}$N$_2$O$_7$S = 444,55 | 83 |

TABLE I-continued

FIRST PROCESS FOR THE SYNTHESIS OF MEDICAMENTS OF FORMULA:

$$Ar-SO_2-NH-(CH_2)_{n+m+1}-\underset{\underset{O}{\|}}{C}-OR_7$$

| no | Ar | n + m + 1 | R₇ | MP °C. | Formula/MW | Reaction yield (%) |
|---|---|---|---|---|---|---|
| 623 | 4-NO₂-C₆H₄ | 3 | " | 94 | $C_{12}H_{16}N_2O_6S = 316,38$ | (88) |
| 563 | " | 5 | " | 83 | $C_{14}H_{20}N_2O_6S = 344,30$ | 89 |
| 610 | " | 10 | " | 71 | $C_{19}H_{30}N_2O_6S = 414,52$ | 66 |
| 679 | 3-NO₂-C₆H₄ | 3 | " | 91 | $C_{12}H_{16}N_2O_6S = 316,33$ | 80 |
| 666 | " | 5 | " | 65 | $C_{14}H_{20}N_2O_6S = 344,39$ | 93 |
| 676 | " | 10 | " | 66 | $C_{19}H_{30}N_2O_6S = 414,52$ | 96 |
| 737 | C₆H₅ | 3 | " | liquide | $C_{12}H_{17}NO_4S = 271,34$ | 97 |
| 750 | " | 5 | " | " | $C_{14}H_{21}NO_4S = 299,40$ | 88 |
| 766 | " | 10 | " | 43 | $C_{19}H_{31}NO_4S = 369,53$ | 99 |
| 739 | 4-CH₃-C₆H₄ | 3 | " | 49 | $C_{13}H_{19}NO_4S = 285,37$ | 95 |
| 752 | " | 5 | " | 47 | $C_{15}H_{23}NO_4S = 313,42$ | 80 |
| 768 | " | 10 | " | 58 | $C_{20}H_{33}NO_4S = 383,56$ | 99 |
| 743 | 4-Cl-C₆H₄ | 3 | " | 84 | $C_{12}H_{16}ClO_4S = 305,79$ | 90 |
| 756 | " | 5 | " | 49 | $C_{14}H_{20}ClNO_4S = 333,85$ | 99 |
| 728 | " | 10 | " | 60 | $C_{19}H_{30}ClNO_4S = 403,98$ | 98 |
| 741 | 4-OCH₃-C₆H₄ | 3 | " | liquide | $C_{13}H_{19}NO_5S = 301,37$ | 99 |
| 754 | " | 5 | " | " | $C_{15}H_{23}NO_5S = 329,42$ | 89 |
| 729 | " | 10 | " | 47 | $C_{20}H_{33}NO_5S = 399,56$ | 89 |

TABLE I-continued

FIRST PROCESS FOR THE SYNTHESIS OF MEDICAMENTS OF FORMULA:

$$Ar-SO_2-NH-(CH_2)_{n+m+1}-\underset{\underset{O}{\|}}{C}-OR_7$$

| no | Ar | n + m + 1 | R7 | MP °C. | Formula/MW | Reaction yield (%) |
|---|---|---|---|---|---|---|
| 745 | 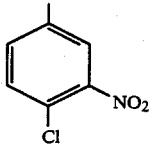 | 3 | " | 79 | $C_{12}H_{15}ClN_2O_6S = 350{,}79$ | 91 |
| 758 | " | 5 | " | 67 | $C_{14}H_{19}Cl_2N_2O_6S = 376{,}55$ | 85 |
| 772 | " | 10 | " | 68 | $C_{19}H_{29}ClN_2O_6S = 448{,}98$ | 87 |
| 784 | 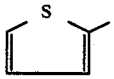 | 3 | " | 46 | $C_{10}H_{15}NO_4S_2 = 277{,}37$ | 84 |
| 802 | " | 5 | " | 42 | $C_{12}H_{19}NO_4S_2 = 305{,}42$ | 78 |
| 806 | " | 10 | " | 54 | $C_{17}H_{29}NO_4S_2 = 375{,}56$ | 91 |
| 852 | 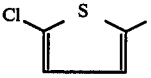 | 5 | butyl | liquide | $C_{14}H_{22}ClNO_4S_2 = 367{,}93$ | 72 |
| 866 | " | 5 | $C_2H_5$ | " | $C_{12}H_{18}ClNO_4S_2 = 339{,}87$ | 68 |
| 867 | " | 3 | " | " | $C_{10}H_{14}ClNO_4S_2 = 311{,}68$ | 75 |
| 853 | 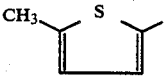 | 3 | " | | $C_{11}H_{17}NO_4S_2 = 291{,}40$ | 83 |
| 787 | 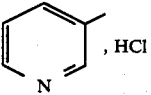 | 3 | " | 111 | $C_{11}H_{17}ClN_2O_4S = 308{,}88$ | 76 |
| 790 | " | 5 | " | 93 | $C_{13}H_{21}ClN_2O_4S = 336{,}83$ | 73 |
| 791 | " | 10 | " | 53 | $C_{18}H_{30}N_2O_4S = 370{,}62$ | 77 |

TABLE I'

FIRST PROCESS FOR THE SYNTHESIS OF COMPOUNDS OF FORMULA:

$$Ar-SO_2-NH-(CH_2)_{n+m+1}-\underset{\underset{O}{\|}}{C}-OR_7$$

| no | Ar | n + m + 1 | R7 | MP °C. | FORMULA/MW | Reaction yield (%) |
|---|---|---|---|---|---|---|
| 784 | 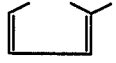 | 3 | $C_2H_5$ | 46 | $C_{10}H_{15}NO_4S_2 = 277{,}37$ | 84 |
| 802 | " | 5 | " | 42 | $C_{12}H_{19}NO_4S_2 = 305{,}42$ | 78 |
| 806 | " | 10 | " | 54 | $C_{17}H_{29}NO_4S_2 = 375{,}56$ | 91 |
| 852 | 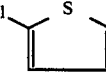 | 5 | butyl | liquide | $C_{14}H_{22}ClNO_4S_2 = 367{,}93$ | 72 |

TABLE I'-continued

FIRST PROCESS FOR THE SYNTHESIS OF COMPOUNDS OF FORMULA:

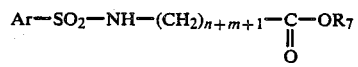

$$Ar-SO_2-NH-(CH_2)_{n+m+1}-\underset{\underset{O}{\|}}{C}-OR_7$$

| no | Ar | n + m + 1 | R7 | MP °C. | FORMULA/MW | Reaction yield (%) |
|---|---|---|---|---|---|---|
| 866 | " | 5 | $C_2H_5$ | " | $C_{12}H_{18}ClNO_4S_2 = 339,87$ | 68 |
| 867 | " | 3 | " | " | $C_{10}H_{14}ClNO_4S_2 = 311,68$ | 75 |
| 853 | 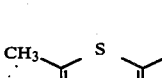 | 3 | " |  | $C_{11}H_{17}NO_4S_2 = 291,40$ | 83 |
| 787 | 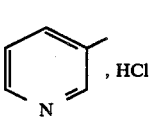 | 3 | " | 111 | $C_{11}H_{17}ClN_2O_4S = 308,88$ | 76 |
| 790 | " | 5 | " | 93 | $C_{13}H_{21}ClN_2O_4S = 336,83$ | 73 |
| 791 |  | 10 | " | 53 | $C_{18}H_{30}N_2O_4S = 370,62$ | 77 |

A second mode of preparation (PROCESS IIA) of the medicaments of formula:

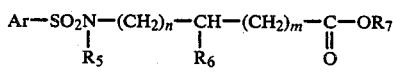

$$Ar-SO_2N-(CH_2)_n-CH-(CH_2)_m-\underset{\underset{O}{\|}}{C}-OR_7$$
with substituents $R_5$, $R_6$ and of the corresponding new compounds, consists in starting from an acid halide, particularly the appropriate acid halide $ArSO_2Cl$ and reacting it with an amino-acid of the formula:

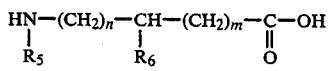

$$HN-(CH_2)_n-CH-(CH_2)_m-\underset{\underset{O}{\|}}{C}-OH$$
with substituents $R_5$, $R_6$ according to the following diagram:

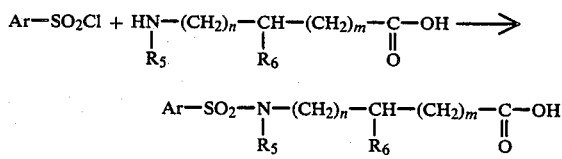

then of esterifying the acid so-obtained, by reacting it with a suitable alcohol of formula $R_7OH$ according to the following diagram:

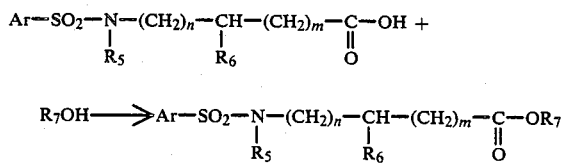

In these formulae, Ar, n, $R_5$, $R_6$ and $R_7$ have the same meanings as those previously indicated.

From the practical point of view, procedure is as follows: the production of the acid takes place in the following manner:

the amino-acid (40 mM) is suspended or solubilized in an anhydrous organic base such as anhydrous pyridine or anhydrous 2,6-dimethylpyridine (15 cm3). The acid chloride (10 mM) is then added in small fractions (or drop by drop); the reaction mixture is stirred vigorously during this addition and kept at a temperature below or equal to 20° C. Then it is heated for one hour at 40° C. and left for 12 hours with stirring at ambient temperature. The pyridine is driven off by concentration under reduced pressure; a cooled solution of dilute acid is added to bring the pH to a value lower than 3, such as dilute hydrochloric acid. If the product precipitates, it is filtered, washed with water, dissolved in a lower alcohol (ethanol or methanol), if necessary decolorized on active charcoal and finally chromatographed. If the product does not precipitate, it is extracted from the medium by ethyl acetate (or any other organic solvent of the same polarity): this phase is dried over sodium sulfate, if necessary decolorized on active charcoal, concentrated under reduced pressure and chromatographed.

A modification has also been followed; it consists of pouring an ethereal solution of acid chloride on the amino-acid in solution in aqueous N caustic soda (ref.: MAC CHESMY, SWAM, J. A. C. S., 59, 1 116).

As for the esterification, it takes place as follows:
the acid ($2 \times 10^{-2}$ mole) is solubilized in 30 cm3 of anhydrous alcohol; perchloric acid is then added (1.5 cm3); then the mixture is heated to 50° C. until the disappearance of the starting product to the profit of the ester.

The following example illustrates the mode of preparing medicaments, for which preparation recourse is had to the above-indicated process in its generality.

EXAMPLE II

Preparation of the ethyl acetate of ε(5-chloro 4-nitro 2-methoxy benzenesulfonamide) caproic acid

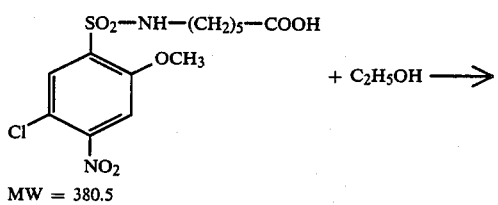

MW = 380.5

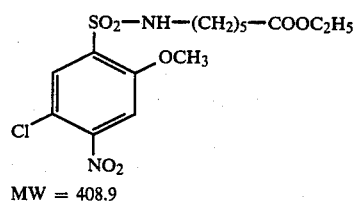

MW = 408.9

The acid (3 g) is stirred magnetically in anhydrous ethanol (10 cm³) in the presence of perchloric acid (2 cm³) at 50° C. for 48 hours (end of reaction checked by thin layer chromatography). The medium was cooled, neutralized with disodium carbonate, extracted with ether. The organic phase was dried over sodium sulfate, then concentrated under reduced pressure. By chromatography on silica H of the residue so-obtained and elution by the mixture benzene/ethyl acetate (4:1), the ethyl ester of (5-chloro 4-nitro 2-methoxy benzenesulfonamide) caproic acid was isolated with a yield of 55%.

The following medicaments were prepared by this process: 380, 486, 502 whose developed chemical formulae are to be found in Table I.

A third method of preparation (PROCESS III/A) of the medicaments as well as the new corresponding compounds of formula:

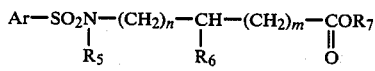

consists in starting from a suitable acid of the formula:

and reacting it on a suitable amino ester of the formula:

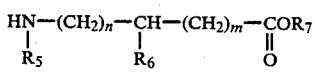

according to the following reaction diagram:

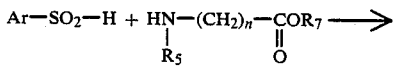

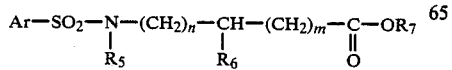

In these formulae corresponding to the medicaments, Ar, n, m, $R_5$, $R_6$ and $R_7$ have the previously indicated meanings.

For the new compounds, Ar, n, m, $R_5$, $R_6$ and $R_7$ have the above said meanings, with the proviso that when Ar represents a benzene nucleus, this latter is substituted by at least a $CF_3$ group.

From a practical point of view, procedure is as follows: an acid solution ($10^{-2}$ mole) solubilized in the minimum of dimethylformamid (DMF) or hexamethylphosphoramide (HMPT) is cooled to $-15°$ C. with magnetic stirring. Successively to this solution were added a N-alkylamine, whose alkyl part has 1 to 4 carbon atoms, and the amine part derives from a tertiary amine such as N-methyl morpholine (1.1 cm3 = $10^{-2}$ mole) and alkyl chloroformate (the alkyl having from 1 to 4 carbon atoms), such as isobutyl chloroformate (1.3 cm3). At the end of 5 minutes, the amino-ester ($10^{-2}$ mole) was poured into the medium in the minimum of DMF (if it relates to the hydrochloride of the amino-ester, it is appropriate to neutralize with N-methyl morpholine (1.1 cm3 = $10^{-2}$ mole). Four hours later, the reaction mixture was poured into a dilute solution of sodium or potassium bicarbonate at 0° C. If the product precipitates, the crystals are washed with water, then dissolved in ethyl acetate and the organic phase washed with a dilute acid, such as hydrochloric acid, to bring the pH to a value lower than 3. After having dried the solution over sodium sulfate, the solvent was evaporated off and the residue so obtained was chromatographed.

A first method for the preparation (PROCESS IB) of the medicaments and new compounds of formula:

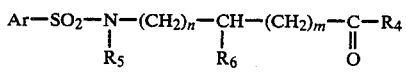

in which $R_4$ represents the hydroxy radical, consists of reacting a suitable acid chloride of formula:

with a suitable amino acid of the formula:

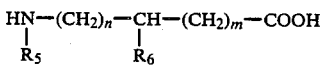

according to the following reaction diagram:

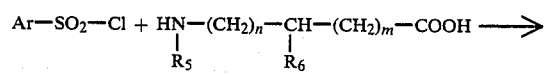

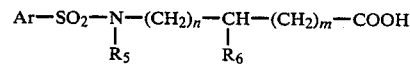

as was previously indicated in the second method of preparation (PROCESS IIA) of the products of the formula:

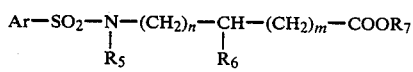

The following examples illustrate the method of preparation of medicaments, for which preparation recourse is had to the above-indicated process in its generality.

EXAMPLE III

Preparation of ε(4-nitro 2-methoxy benzenesulfonamido)caproic acid.

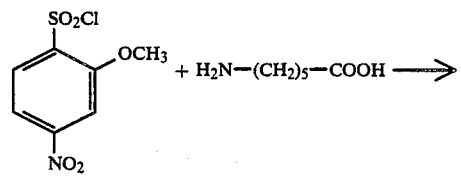

MW = 254.5    MW = 131

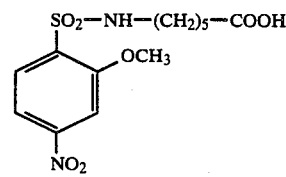

MW = 318.3

To ε-amino caproic acid ($5 \times 10^{-2}$ mole = 6.55 g) in pyridine (150 cm³), with magnetic stirring and kept at a temperature of about 20° C. by water bath, was added in small fractions 2-methoxy 4-nitro benzenesulfonyl chloride ($2 \times 10^{-2}$ mole = 5.08 g).

After the addition, the reaction mixture was heated for one hour at 40° C. The solvent was evaporated and the residue so-obtained was washed with 3% hydrochloric acid (200 cm³) then extracted with ethyl acetate (400 cm³, then twice 100 cm³). The organic phases were combined, dried over sodium sulfate and concentrated under reduced pressure. The product was solubilized in methanol, decolorized on activated charcoal, concentrated and chromatographed on silica H by the eluant toluene/ethyl acetate/acetic acid (80:20:2).

The fractions containing the ε(4nitro 2-methoxybenzenesulfonamido) caproic acid were concentrated and the compound was recrystallized in a water/ethanol mixture (yield 50%).

EXAMPLE IV

Preparation of (trifluoromethyl-3 benzenesulfonylamino)-4 butyric acid

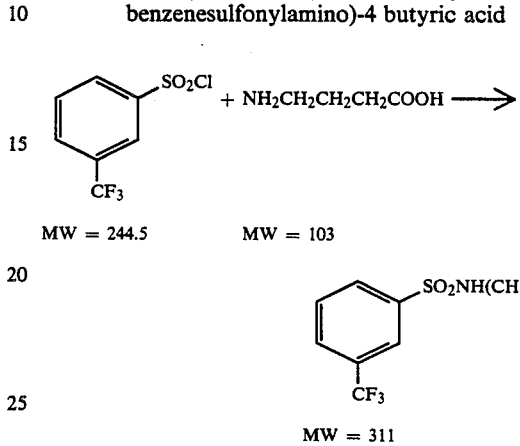

MW = 244.5    MW = 103

MW = 311

Trifluoromethyl-benzenesulfonyl chloride ($2 \times 10^{-2}$ mole: 4.89 g) is added dropwise to ω-aminobutyric acid ($5 \times 10^{-2}$ mole = 5.15 g) into pyridine (100 cm3) under magnetic stirring and maintained at a temperature of about 20° C. in a water bath.

After addition, the reaction mixture is heated for one hour at 40° C. The solvent is evaporated and the residue thus obtained is collected in 100 cm3 of water. The solution is then brought to a pH of 2.3 by addition of hydrochloridric acid 2N.

The precipitate is centrifuged, then dried and recrystallized in benzene (yield 42%).

The following medicaments assembled in Table II below were prepared by the process, as well as the new compounds, gathered in the Table II' hereafter.

TABLE II

PREPARATION OF MEDICAMENTS OF FORMULA:

$$Ar-SO_2-NH-(CH_2)_n-CH_2-(CH_2)_m-\underset{\underset{O}{\|}}{C}-OR_7$$

| no | Ar | n + m + 1 | R7 | MP °C. | FORMULA/MW | Reaction yield (%) |
|---|---|---|---|---|---|---|
| 387 | 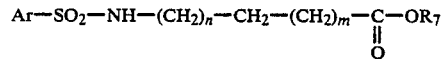 | 3 | H | 130 | $C_{11}H_{13}ClN_2O_7S$ = 352.75 | 16 |
| 362 | " | 5 | " | 145 | $C_{13}H_{17}ClN_2O_7S$ = 380.80 | 17 |
| 504 | " | 7 | " | 126 | $C_{15}H_{21}ClN_2O_7S$ = 408.86 | 31 |
| 501 | " | 10 | " | 126 | $C_{18}H_{27}ClN_2O_7S$ = 450.94 | 72 |
| 660 | | 3 | " | 135 | $C_{11}H_{14}N_2O_7S$ = 318.30 | 32 |

TABLE II-continued

PREPARATION OF MEDICAMENTS OF FORMULA:

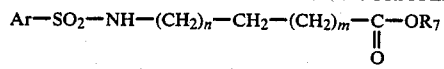

| no | Ar | n + m + 1 | R$_7$ | MP °C. | FORMULA/MW | Reaction yield (%) |
|---|---|---|---|---|---|---|
| 696 | " | 5 | " | 134 | $C_{13}H_{18}N_2O_7S$ = 346.36 | 50 |
| 661 | " | 10 | " | 121 | $C_{18}H_{28}N_2O_7S$ = 416.49 | 52 |
| 548 | 4-NO$_2$-C$_6$H$_4$- | 3 | " | 145 | $C_{10}H_{12}N_2O_6S$ = 288.28 | 19 |
| 562 | " | 5 | " | 130 | $C_{12}H_{16}N_2O_6S$ = 316.33 | 35 |
| 564 | " | 10 | " | 104 | $C_{17}H_{26}N_2O_6S$ = 386.47 | 51 |
| 674 | 3-NO$_2$-C$_6$H$_4$- | 3 | " | 120 | $C_{10}H_{12}N_2O_6S$ = 288.28 | 42 |
| 675 | " | 5 | " | 115 | $C_{12}H_{16}N_2O_6S$ = 316.33 | 67 |
| 697 | " | 10 | " | 120 | $C_{17}H_{26}N_2O_6S$ = 386.47 | 72 |
| 1038 | 3-CF$_3$-C$_6$H$_4$- | 3 | " | 116 | $C_{11}H_{12}F_3NO_4S$ = 311.29 | 41 |
| 786 | 3-pyridyl | 3 | " | 150 | $C_9H_{12}N_2O_4S$ = 244.28 | 38 |

TABLE II'

PREPARATION OF COMPOUNDS OF FORMULA:

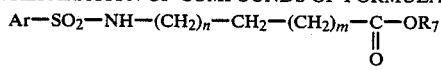

| no | Ar | n + m + 1 | R$_7$ | MP °C. | FORMULA/MW | Reaction yield (%) |
|---|---|---|---|---|---|---|
| 1038 | 3-CF$_3$-C$_6$H$_4$- | 3 | H | 116 | $C_{11}H_{12}F_3NO_4S$ = 311 | 41 |
| 786 | 3-pyridyl | 3 | " | 140 | $C_9H_{12}N_2O_4S$ = 244.28 | 38 |

A modification of the procedure described in Example III consists in pouring acid chloride in solution in an organic solvent, inert with respect to acid chloride and non miscible with water, such as chloroform, dioxanne, benzene, toluene, preferably ether onto the amino-acid in an aqueous solution such as aqueous sodium hydroxyde or aqueous potassium hydroxyde (ref. MAC CHESMY, SWAM, JACS, 59, 1 116).

The following example illustrates this embodiment.

Preparation of compound no. 1038

The medicaments collected in Table III below were prepared by the process, as well as the new compounds gathered in the following Table III'.

TABLE III

| no | Ar | n + m + 1 | R₇ | MP °C. | FORMULA/MW | Reaction yield (%) |
|---|---|---|---|---|---|---|
| 1038 | 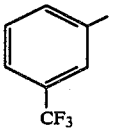 | 3 | H | 116 | $C_{11}H_{12}F_3NO_4S$ = 311.29 | 72 |
| 1150 | 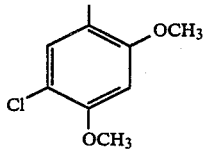 | 3 | " | 166 | $C_{12}H_{16}ClNO_6S$ = 337.8 | 65 |
| 1151 | 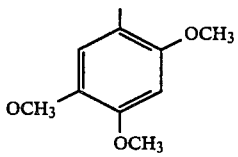 | 3 | " | 177 | $C_{12}H_{19}NO_7S$ = 321.36 | 70 72 |

TABLE III'

| no | Ar | n + m + 1 | R₇ | MP °C. | FORMULA/MW | Reaction yield (%) |
|---|---|---|---|---|---|---|
| 1038 | 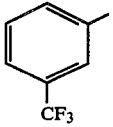 | 3 | H | 116 | $C_{11}H_{12}F_3NO_4S$ = 311.29 | 41 |
| 1129 | " | 5 | H | 96 | $C_{13}H_{16}F_3NO_4S$ = 339.35 | 90 |

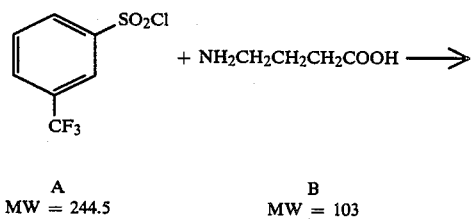

A
MW = 244.5

B
MW = 103

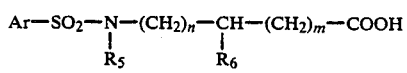

C
MW = 311

To 1.545 g (0.015 mole) of 4-amino butyric acid in 30 cm³ of N soda, was added drop by drop with vigorous stirring, a solution of 3.7 g (0.015 mole) of trifluoro 3 methyl benzene sulfochloride in 30 cm³ of ethyl ether.

After 4 hours stirring, the organic phase was removed. The aqueous phase was then brought to pH 3 with 2N hydrochloric acid. The precipitate formed was drained, washed with water until the Cl⁻ ion was absent and then dried.

A second method of preparation (PROCESS IIB) of the medicaments and of new compounds according to the invention, of the formula:

$$Ar-SO_2-N(R_5)-(CH_2)_n-CH(R_6)-(CH_2)_m-COOH$$

consists in preparing:

in a first step, as ester of the acid that it is desired to obtain, by one of the two processes IA or IIA which have been considered above, for the synthesis of medicaments and new compounds of formula:

$$Ar-SO_2-N(R_5)-(CH_2)_n-CH(R_6)-(CH_2)_m-COOR_7$$

then in a second step, hydrolysing the ester obtained into its corresponding acid according to the diagram:

$$Ar-SO_2-N(R_5)-(CH_2)_n-CH(R_6)-(CH_2)_m-COOR_7 \longrightarrow$$

-continued $$Ar-SO_2-N-(CH_2)_n-CH-(CH_2)_m-COOH$$
$$\phantom{Ar-SO_2-N}|\phantom{(CH_2)_n-}|$$
$$\phantom{Ar-SO_2-N}R_5\phantom{(CH_2)_n-}R_6$$

From a practical point of view, operation is as follows: $10^{-2}$ mole of ester in 50 cm3 of 1N–5N alkaline or earth alkaline base in an alcoholic medium, the corresponding alcohol of which having from 1 to 4 carbon atoms, preferably 1N–5N ethanolic soda, and more particularly 2N ethanolic soda was stirred magnetically for 12 hours at room temperature. The reaction medium was neutralized in the cold with an acid to bring the pH to a value lower than 3, for instance with concentrated 2N–10N hydrochloric acid and extracted with an organic solvent, non miscible with water such as ethyl acetate. The organic phase was washed with water, dried over sodium sulfate and concentrated under reduced pressure.

The following example illustrates the method of preparing the medicaments and new compounds according to the invention, for which preparation recourse was had to the above indicated method in its generality.

EXAMPLE VI

Preparation of the compound no. 744

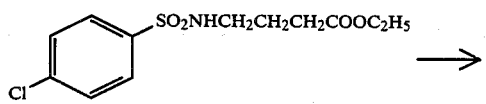

A 743
MW = 305.5

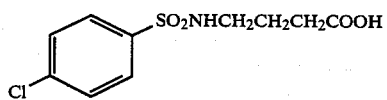

B
MW = 277.5

The ester A (120 g) was suspended in a mixture of 2N soda (400 cm³) and 300 cm³ of ethanol.

After one night with magnetic stirring at room temperature, the reaction medium was evaporated to dryness under vacuum, the residue was taken up again in 200 cm³ of water, then brought to pH 3 by the addition of 2N hydrochloric acid. The precipitate was drained, washed with water until the Cl⁻ ion was absent and then dried under vacuum. The yield was 86%.

EXAMPLE VII

Preparation of (trifluoromethyl-3 benzenesulfonylamino)-6 hexanoic acid

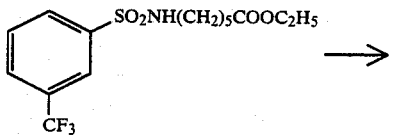

A
MW = 367,3

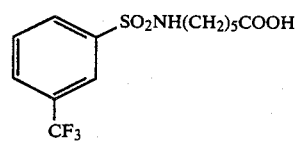

B
MW = 339,3

The ester A ($2\times10^{-2}$ mole = 7.35 g) is suspended in a mixture of sodium hydroxyde 2N (20 cm3) and ethanol (10 cm3).

After a night, under magnetic stirring, at room temperature, the reaction mixture is evaporated under vaccum in dried conditions.

The residue is collected in 30 cm3 of water then brought to a pH of 8 by addition of hydrochloridric acid 2N. The precipitate is dried, washed with water until Cl⁻ ions disappear, then is dried under vacuum (yield 80%).

The following medicaments collected in Table IV below were prepared by this method, as well as the new compounds gathered in the Table IV' hereafter.

TABLE IV

PREPARATION OF MEDICAMENTS OF FORMULA:
$Ar-SO_2-NH-(CH_2)_n-CH_2-(CH_2)_m-COOR_7$

| no | Ar | n + m + 1 | R7 | MP °C. | FORMULA/MW | Reaction yield (%) |
|---|---|---|---|---|---|---|
| 387 | ![Ar with OCH3, Cl, NO2] | 3 | H | 130 | $C_{11}H_{13}ClN_2O_7S = 352.75$ | 99 |
| 789 | " | 4 | " | 95 | $C_{12}H_{15}ClN_2O_7S = 366.79$ | 95 |
| 362 | " | 5 | " | 145 | $C_{13}H_{17}ClN_2O_7S = 380.80$ | 96 |
| 854 | ![Ar with OCH3, Cl, NH2] | 4 | " | 128 | $C_{12}H_{13}ClN_2O_5S = 332.78$ | 85 |

TABLE IV-continued

PREPARATION OF MEDICAMENTS OF FORMULA:
$Ar-SO_2-NH-(CH_2)_n-CH_2-(CH_2)_m-COOR_7$

| no | Ar | n + m + 1 | R7 | MP °C. | FORMULA/MW | Reaction yield (%) |
|---|---|---|---|---|---|---|
| 738 |  | 3 | " | 90 | $C_{10}H_{13}NO_4S$ = 243.29 | 99 |
| 751 | " | 5 | " | 121 | $C_{12}H_{17}NO_4S$ = 271.34 | 99 |
| 767 | " | 10 | " | 95 | $C_{17}H_{27}NO_4S$ = 341.48 | 95 |
| 740 |  CH3 | 3 | " | 135 | $C_{11}H_{15}NO_4S$ = 257.32 | 94 |
| 753 | " | 5 | " | 111 | $C_{13}H_{19}NO_4S$ = 285.37 | 87 |
| 769 | " | 10 | " | 90 | $C_{18}H_{29}NO_4S$ = 355.50 | 95 |
| 744 | 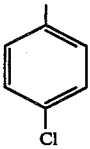 Cl | 3 | " | 134 | $C_{10}H_{12}ClNO_4S$ = 277.74 | 97 |
| 757 | " | 5 | " | 130 | $C_{12}H_{16}ClNO_4S$ = 305.79 | 95 |
| 771 | " | 10 | " | 126 | $C_{17}H_{26}ClNO_4S$ = 375.93 | 89 |
| 1129 | 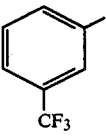 CF3 | 5 | " | 96 | $C_{13}H_{16}F_3NO_4S$ = 339.35 | 80 |
| 742 | 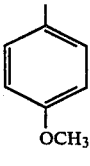 OCH3 | 3 | " | 110 | $C_{11}H_{15}NO_5S$ = 273.32 | 99 |
| 755 | " | 5 | " | 89 | $C_{13}H_{19}NO_5S$ = 301.37 | 96 |
| 770 | " | 10 | " | 98 | $C_{18}H_{29}NO_5S$ = 371.50 | 96 |
| 746 | 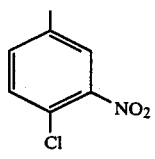 NO2 Cl | 3 | " | 135 | $C_{10}H_{11}ClN_2O_6S$ = 322.74 | 91 |
| 759 | " | 5 | " | 119 | $C_{12}H_{15}ClN_2O_6S$ = 350.79 | 99 |
| 792 | " | 10 | " | 115 | $C_{17}H_{25}ClN_2O_6S$ = 420.93 | 86 |
| 800 | 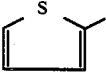 S | 5 | " | 112 | $C_{10}H_{15}NO_4S_2$ = 277.37 | 80 |
| 823 | " | 10 | " | 91 | $C_{15}H_{25}NO_4S_2$ = 347.51 | 90 |

TABLE IV-continued

PREPARATION OF MEDICAMENTS OF FORMULA:
$Ar-SO_2-NH-(CH_2)_n-CH_2-(CH_2)_m-COOR_7$

| no | Ar | n + m + 1 | $R_7$ | MP °C. | FORMULA/MW | Reaction yield (%) |
|---|---|---|---|---|---|---|
| 785 |  | 3 | " | 140 | $C_9H_{12}N_2O_4S = 244.28$ | 85 |
| 804 | " | 5 | " | 124 | $C_{11}H_{16}N_2O_4S = 272.33$ | 82 |
| 824 | " | 10 | " | 110 | $C_1H_{26}N_2O_4S = 342.47$ | 91 |

TABLE IV'

PREPARATION OF COMPOUNDS OF FORMULA:
$Ar-SO_2-NH-(CH_2)_n-CH_2-(CH_2)_m-COOR_7$

| no | Ar | n + m + 1 | $R_7$ | MP °C. | FORMULA/MW | Reaction yield (%) |
|---|---|---|---|---|---|---|
| 1 129 | 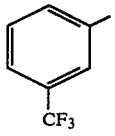 | 5 | H | 96 | $C_{13}H_{16}F_3NO_4S = 339.35$ | 80 |
| 800 |  | 5 | " | 112 | $C_{10}H_{15}NO_4S_2 = 277.37$ | 80 |
| 823 | " | 10 | " | 91 | $C_{15}H_{25}NO_4S_2 = 347.51$ | 90 |
| 785 | 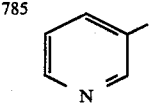 | 3 | H | 140 | $C_9H_{12}N_2O_4S = 244.28$ | 85 |
| 804 | " | 5 | " | 124 | $C_{11}H_{16}N_2O_4S = 272.33$ | 82 |
| 824 | " | 10 | " | 110 | $C_{16}H_{26}N_2O_4S = 342.47$ | 91 |

A method of preparing medicaments, according to the invention, of the formula:

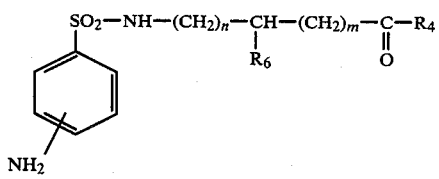

in which
$R_4$ represents:
the hydroxy group,
the group $OR_7$, $R_7$ being an alkyl radical of 1 to 6 carbon atoms,
consists in using, as starting material, the medicament of the formula:

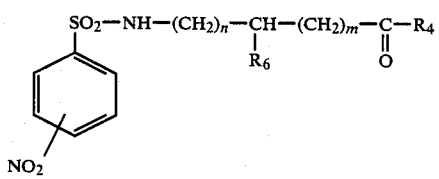

and subjecting it to catalytic hydrogenation.

From a practical point of view, the ester of the acid is placed in solution in ethyl acetate which is stirred magnetically, under a hydrogen atmosphere, in the presence of palladized charcoal, the amount of catalyst being 5% in the case where the starting medicament is an acid and 10% when it is an ester. After four hours, the hydrogen absorption is finished, the catalyst is filtered and the filtrate is concentrated under reduced pressure.

The following example illustrates the method of preparing medicaments, according to the invention, for which preparation recourse is had to the above-indicated process in its generality.

EXAMPLE VIII

Preparation of ε(4-amino 2-methoxy benzenesulfonamido) caproic acid

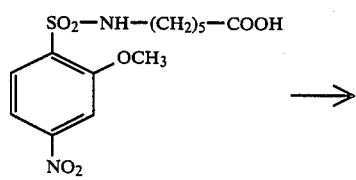

MW = 346.36

-continued

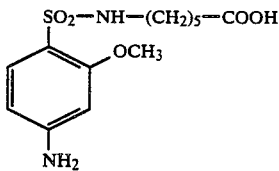

MW = 316.38

A solution of ϵ(4-nitro 2-methoxy-benzenesulfonamido) caproic acid (1.4 g) in solution in ethyl acetate (150 cm³) is stirred magnetically under a hydrogen atmosphere in the presence of 5% palladized charcoal (120 mg). After four hours, the hydrogen absorption being terminated, the catalyst is filtered and the filtrate concentrated under reduced pressure. Pure ϵ(4-amino 2-methoxy-benzenesulfonamido) caproic acid is obtained, with a yield of 98%.

The following medicaments collected in Table V below were prepared by resorting to this method of preparation.

TABLE V

PREPARATION OF COMPOUNDS OF FORMULA:

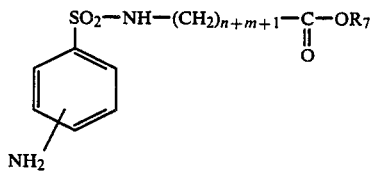

| no | Ar | n+m+1 | R₇ | MP °C. | FORMULA/MW | Reaction yield [%] |
|---|---|---|---|---|---|---|
| 484 | 5-Cl, 2-OCH₃, 4-NH₂·HCl phenyl | 3 | $C_2H_5$ | 137 | $C_{13}H_{20}Cl_2N_2O_5S$ = 387.28 | 84 |
| 748 | 5-Cl, 2-OCH₃, 4-NH₂·HCl phenyl | 3 | H | 127 | $C_{11}H_{15}ClN_2O_5S$ = 322.78 | 77 |
| 788 | 5-Cl, 2-OCH₃, 4-NH₂·TsOH phenyl | 4 | $C_2H_5$ | 164 | $C_{21}H_{29}ClN_2O_8S_2$ = 537.07 | 92 |
| 469 | 5-Cl, 2-OCH₃, 4-NH₂·HCl phenyl | 5 | $C_2H_5$ | 133 | $C_{15}H_{24}Cl_2N_2O_5S$ = 415.34 | 83 |
| 763 | 5-Cl, 2-OCH₃, 4-NH₂·HCl phenyl | 5 | H | 92 | $C_{13}H_{19}ClN_2O_5S$ = 350.83 | 94 |
| 730 | 5-Cl, 2-OCH₃, 4-NH₂·TsOH phenyl | 7 | $C_2H_5$ | 124 | $C_{24}H_{35}ClN_2O_8S_2$ = 579.11 | 61 |

TABLE V-continued
PREPARATION OF COMPOUNDS OF FORMULA:

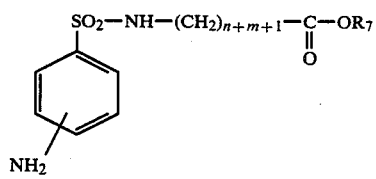

| no | Ar | n+m+1 | R$_7$ | MP °C. | FORMULA/MW | Reaction yield [%] |
|---|---|---|---|---|---|---|
| 503 | 4-CH$_3$, 5-OCH$_3$, 2-Cl, NH$_2$, TsOH phenyl | 10 | C$_2$H$_5$ | 132 | C$_{27}$H$_{41}$ClN$_2$O$_8$S = 621.21 | 66 |
| 805 | 4-CH$_3$, 5-OCH$_3$, 2-Cl, NH$_2$, TsOH phenyl | 10 | H | 100 | C$_{18}$H$_{29}$ClN$_2$O$_5$S = 420.97 | 90 |
| 656 | 4-CH$_3$, 3-OCH$_3$, NH$_2$, TsOH phenyl | 3 | C$_2$H$_5$ | 187 | C$_{20}$H$_{28}$N$_2$O$_8$S$_2$ = 487.78 | 98 |
| 612 | 4-CH$_3$, 3-OCH$_3$, NH$_2$, TsOH phenyl | 5 | C$_2$H$_5$ | 188 | C$_{22}$H$_{32}$N$_2$O$_8$S$_2$ = 516.63 | 57 |
| 694 | 4-CH$_3$, 3-OCH$_3$, NH$_2$, TsOH phenyl | 5 | H | 116 | C$_{13}$H$_{20}$N$_2$O$_5$S = 316.38 | 100 |
| 627 | 4-CH$_3$, 3-OCH$_3$, NH$_2$, TsOH phenyl | 10 | C$_2$H$_5$ | 80 | C$_{20}$H$_{34}$N$_2$O$_5$S = 414.57 | 100 |
| 668 | 4-CH$_3$, 3-OCH$_3$, NH$_2$, TsOH phenyl | 10 | H | 105 | C$_{18}$H$_{30}$N$_2$O$_5$S = 386.51 | 94 |

TABLE V-continued

PREPARATION OF COMPOUNDS OF FORMULA:

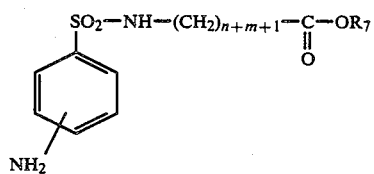

| no | Ar | n+m+1 | R$_7$ | MP °C. | FORMULA/MW | Reaction yield [%] |
|---|---|---|---|---|---|---|
| 624 | 4-NH$_2$-C$_6$H$_4$-, TsOH | 3 | C$_2$H$_5$ | 158 | C$_{19}$H$_{26}$N$_2$O$_7$S$_2$ = 458.55 | 99 |
| 609 | 4-NH$_2$-C$_6$H$_4$-, TsOH | 5 | C$_2$H$_5$ | 86 | C$_{14}$H$_{22}$N$_2$O$_4$S = 314.40 | 96 |
| 665 | 4-NH$_2$-C$_6$H$_4$-, TsOH | 5 | H | 131 | C$_{12}$H$_{18}$N$_2$O$_4$S = 286.35 | 97 |
| 626 | 4-NH$_2$-C$_6$H$_4$-, TsOH | 10 | C$_2$H$_5$ | 85 | C$_{19}$H$_{32}$N$_2$O$_4$S = 384.54 | 100 |
| 667 | 4-NH$_2$-C$_6$H$_4$-, TsOH | 10 | H | 118 | C$_{17}$H$_{28}$N$_2$O$_4$S = 358.49 | 88 |
| 680 | 3-NH$_2$-C$_6$H$_4$- | 3 | H | 99 | C$_{10}$H$_{14}$N$_2$O$_4$S = 258.30 | 100 |
| 693 | 3-NH$_2$-C$_6$H$_4$-, TsOH | 3 | C$_2$H$_5$ | 144 | C$_{19}$H$_{25}$N$_2$O$_7$S$_2$ = 458.55 | 97 |
| 681 | 3-NH$_2$-C$_6$H$_4$- | 5 | H | 86 | C$_{12}$H$_{18}$N$_2$O$_4$S = 286.35 | 100 |

TABLE V-continued

PREPARATION OF COMPOUNDS OF FORMULA:

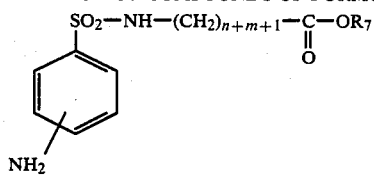

| no | Ar | n+m+1 | R$_7$ | MP °C. | FORMULA/MW | Reaction yield [%] |
|---|---|---|---|---|---|---|
| 682 | ![3-aminophenyl, TsOH] | 5 | C$_2$H$_5$ | 109 | C$_{21}$H$_{30}$N$_2$O$_7$S$_2$ = 486.51 | 93 |
| 683 | ![3-aminophenyl] | 10 | C$_2$H$_5$ | 56 | C$_{19}$H$_{32}$N$_2$O$_4$S = 384,54 | 96 |
| 695 | ![3-aminophenyl] | 10 | H | 105 | C$_{17}$H$_{28}$N$_2$O$_4$S = 356.49 | 99 |
| 747 | ![3-amino-4-chlorophenyl, Cl, TsOH] | 3 | C$_2$H$_5$ | 174 | C$_{19}$H$_{25}$ClN$_2$O$_7$S$_2$ = 493.01 | 57 |
| 785 | ![3-amino-4-chlorophenyl] | 3 | H | 71 | C$_{10}$H$_{13}$ClN$_2$O$_4$S = 292.75 | 89 |
| 760 | ![3-amino-4-chlorophenyl, TsOH] | 5 | C$_2$H$_5$ | 147 | C$_{21}$H$_{29}$ClN$_2$O$_7$S$_2$ = 521.07 | 79 |
| 761 | ![3-amino-4-chlorophenyl] | 5 | H | 83 | C$_{12}$H$_{17}$ClN$_2$O$_4$S = 320.81 | 80 |
| 773 | ![3,4-diaminophenyl, NH$_2$, TsOH] | 10 | C$_2$H$_5$ | 138 | C$_{26}$H$_{39}$ClN$_2$O$_7$S$_2$ = 591.20 | 80 |

A method for the preparation of the medicaments and new compounds of formula:

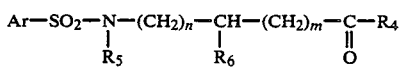

from:

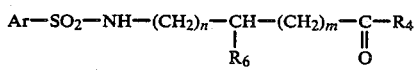

in which formulae $R_4$ represents OH or an alkoxy radical of 1 to 6 carbon atoms, with the proviso, for the new compounds, that when Ar represents a benzene nucleus, this latter is substituted by at least one $CF_3$ radical, consists of reacting an alkyl halide such as an alkyl iodide $R_5I$ according to the following plan:

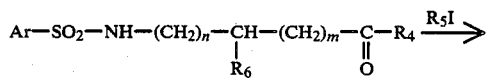

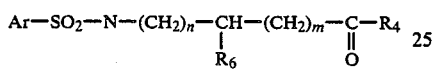

From a practical point of view, procedure is as folows:

The sulfonylamino acid (1 mM) is dissolved by the addition of an excess of a strong aqueous base (caustic soda, caustic potash). The alkylation agent may be an alkyl or aralkyl halide (the halide being an chloride, bromide, or iodide) or an alkyl sulfate (dimethylsulfate, diethylsulfate).

This alkylation agent is added drop by drop in the cold, the pH of the reaction being, if necessary, kept at a value above or equal to 10.

After heating the reaction medium from 3 to 24 h, according to the agent and at a temperature comprised between 60° and 100° C., the aqueous phase was extracted after cooling with a non-miscible solvent (ether, TMF, benzene, ethyl acetate), preferably ether.

The aqueous phase was then brought to pH≦3 by the addition of an inorganic acid (hydrochloric, hydrobromic, sulfuric acid), preferably hydrochloric acid.

The precipitate was drained and recrystallized in a suitable organic or aqueous solvent.

The following Example illustrates the method of preparing medicaments, for which preparation recourse is had to the above-indicated process in its generality.

EXAMPLE IX

Preparation of the compound no. 1 045

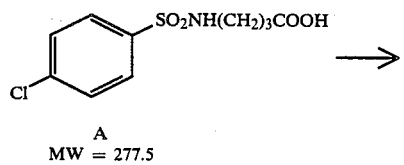

A
MW = 277.5

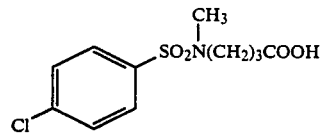

B
MW = 291.5

To 6.2 g (2.23×10⁻² mole) of the product A in 55 cm³ of a solution of N sodium hydroxide, 8 g of methyl iodide were added drop by drop with stirring.

The reaction mixture was brought for five hours to 80° C. The aqueous phase after cooling was extracted with ether. The organic phase was eliminated, the aqueous phase was then brought to pH 3 with 2N hydrochloric acid. The precipitate formed was drained, washed with water and then dried. After recrystallization from a mixture benzene 1:cyclohexane:1, 5.85 g of crystals melting at 121° were collected (Yield 90%).

This method of alkylation was applied to other sulfonamido acids and enabled in particular the preparation of the compound no. 1044:N-methyl 3'-nitro 4-benzenesulfonamido butyric acid.

EXAMPLE X

Methylation of (trifluoromethyl-3 benzenesulfonylamino)-4 butyric acid (compound no. 1 038)

SO₂—NH—(CH₂)₃—COOH

→ methyl iodide

MW = 311
compound no 1 038

SO₂—N—(CH₂)₃—COOH
   |
   CH₃

CF₃

MW = 325
compound no 1 174

4 g of methyl iodide are added dropwise under stirring to 3.1 g of (trifluoromethyl-3 benzenesulfonylamino)-4 butyric acid (1×10⁻² mole) in 30 cm3 of sodium hydroxyde N.

The reaction mixture is brought for four hours at 80° C. The aqueous phase is extracted after cooling with ether. The organic phase is eliminated. The aqueous phase is then brought to a pH of 3 with hydrochlorhydric acid 2N.

The precipitate is centrifugated, washed with water and dried.

The melting point of the compound obtained (compound no. 1 174) is 115 and the yield is 80%.

A method for preparing medicaments and new compounds of the formula:

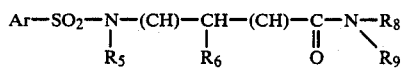

in which $R_5$, $R_6$, $R_8$ and $R_9$ have the above-indicated meanings, starting from:

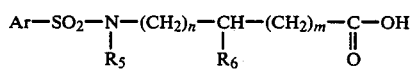

consists of:
reacting thionyl chloride with the acid according to the following reaction diagram:

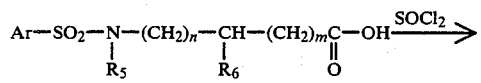

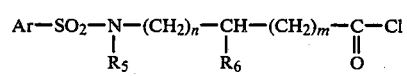

then reacting with the acid chloride, the appropriate amine according to the reaction diagram:

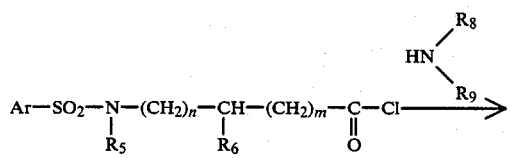

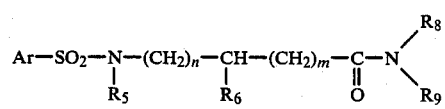

From a practical point of view, operation is as follows.

The acid is dissolved in anhydrous benzene and an excess of thionyl chloride is added. After reflux, the reaction mixture was evaporated to dryness and the residue was taken up again in the appropriate amine. After heating between 40° and 60° C., the reaction mixture was taken up again in ethyl acetate. The organic phase washed with 2N hydrochloric acid and then with water, then with a sodium carbonate solution, was evaporated to give a crystalline residue corresponding to the amide.

The following Example illustrates the method of preparing medicaments according to the invention, for which preparation recourse is had to the above-indicated process in its generality.

EXAMPLE XI

Preparation of the compound no. 1 031

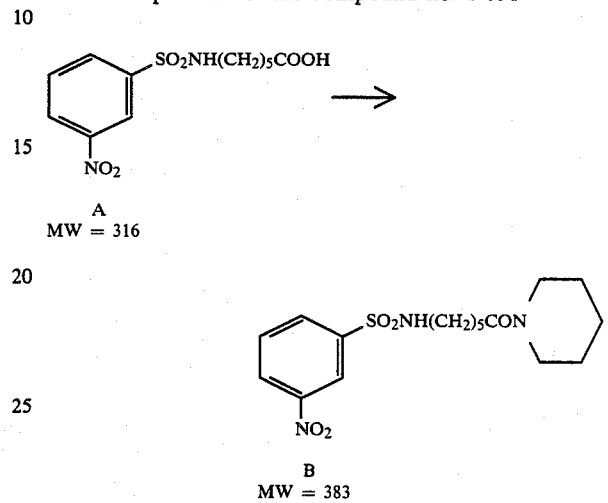

To 3.16 g (0.01 mole) of the acid A in 20 cm³ of anhydrous benzene is added 0.85 ml (1.43 g namely 0.012 mole) of distilled thionyl chloride. The reaction medium was brought to 60° C. for five hours. After evaporation to dryness under vacuum, the residue was taken up in 10 cm³ of benzene, then 10 cm³ of freshly distilled piperidine was added drop by drop. The reaction medium was then brought to 70° C. for two hours, then evaporated to dryness under vacuum. The residue was dissolved in 150 cm³ of ethyl acetate. The organic phase obtained was washed with water, then with N hydrochloric acid, then with water, and was dried over sodium sulfate. The crystals obtained by evaporation were recrystallized from benzene (3 g yield: 78%).

The new compounds as well as the medicaments have been prepared according to example XI and gathered in the following Table VI.

In this case, the medicaments according to the invention are all new compounds.

TABLE VI

| no | Ar | n+m+1 | $R_4$ | MP °C. | FORMULA/MW | Reaction yield [%] |
|---|---|---|---|---|---|---|
| 1 029 | 3-NO$_2$-C$_6$H$_4$ | 5 | N(H)(H) | 103 | $C_{12}H_{17}N_3O_5S = 315{,}36$ | 48 |
| 1 030 | 3-NO$_2$-C$_6$H$_4$ | 5 | N(C$_2$H$_5$)(C$_2$H$_5$) | 54 | $C_{16}H_{25}N_3O_5S = 371{,}47$ | 54 |

TABLE VI-continued

| no | Ar | n+m+1 | R4 | MP °C. | FORMULA/MW | Reaction yield [%] |
|---|---|---|---|---|---|---|
| 1 031 | 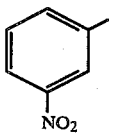 | 5 |  | 80 | $C_{17}H_{25}N_3O_5S = 383,48$ | 78 |
| 1 032 | 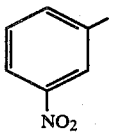 | 5 |  | 80 | $C_{16}H_{23}N_3O_6S = 385,45$ | 52 |
| 1 130 | 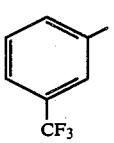 | 5 |  | 102 | $C_{18}H_{25}F_2N_2O_3S = 406,48$ | 73 |
| 1 168 | 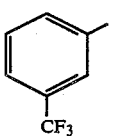 | 5 | 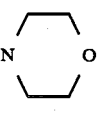 | 120 | $C_{17}H_{23}F_3N_2O_4S = 408,45$ | 70 |
| 1 170 | 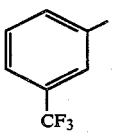 | 5 |  | 66 | $C_{17}H_{25}F_3N_2O_3S = 394,45$ | 72 |
| 1 171 | 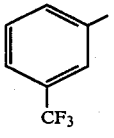 | 5 |  | 104 | $C_{13}H_{17}F_3N_2O_3S = 338,36$ | 66 |
| 1 176 | 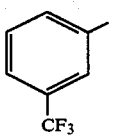 | 3 | 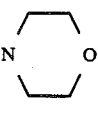 | 91 | $C_{15}H_{19}F_3N_2O_4S = 380.39$ | 70 |
| 1 177 | 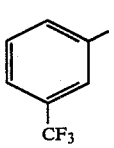 | 3 |  | 95 | $C_{16}H_{21}F_3N_2O_3S = 378.48$ | 72 |
| 1 178 | 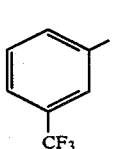 | 3 |  | 108 | $C_{11}H_{13}F_3N_2O_3S = 319.30$ | 60 |

The chemical compounds, above defined according to the invention as well as their phsyiologically acceptable salts, may enter, as active substances, into the preparation of medicaments having a group of pharmacological and therapeutic properties of high value.

Among the physiologically acceptable salts of the compounds according to the invention, may be mentioned particularly:
as regards the salts formed from an acid:
the alkali or alkaline earth salts;

or salts of an organic base such as the meglumate, aceglumate;

as regards the anions:

the hydrochlorides, hydrobromides, sulfates, phosphates, methanesulfonates, tosylates, tartrates, acetates, fumarates, succinate, pyruvate, phenoxyacetate and chlofibrate.

The salts of the medicaments according to the invention are:

1. either salts formed from the salification of the carboxylic group —COOH in the compounds of the formula:

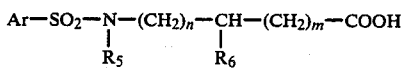

$$Ar-SO_2-N-(CH_2)_n-CH-(CH_2)_m-COOH$$
$$\phantom{Ar-SO_2-}R_5\phantom{-(CH_2)_n-}R_6$$

2. or the salts formed from the salification by a base of the group —NH in the compounds of the formula:

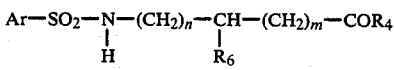

$$Ar-SO_2-N-(CH_2)_n-CH-(CH_2)_m-COR_4$$
$$\phantom{Ar-SO_2-}H\phantom{-(CH_2)_n-}R_6$$

3. or the salts formed from salification of the radical

in the compounds of the formula:

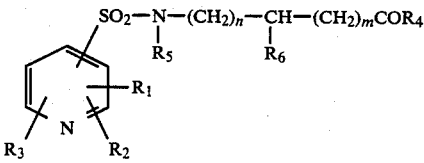

4. or the salts from the compounds with salification of the substituent amino group of the aromatic nucleus in the compounds of the formula:

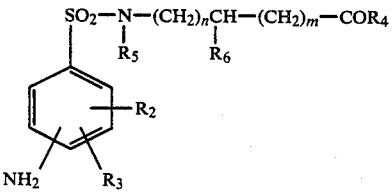

In the first case, the unsalified compound is changed into the salt by reacting in equimolecular amount and in manner known in itself, the base and the selected product.

In the second case, the unsalified compound is changed into the salt by reacting in equimolecular amount and in manner known in itself, the base and the selected product.

In the third and fourth cases, the unsalified compound is changed into the salt by reacting in equimolecular amount and in manner known in itself, the acid and the selected product.

The medicaments according to the invention have remarkable properties in the field of disorders of lipemia.

LIPID REGULATING ACTIVITY

1. Triton test

In a first series of experiments, products were tested on a hyperlipidemia caused by the administration of TRITON according to the following procedure.

The tests were carried out on groups of five WISTAR male rats whose weight varied from 150 to 175 g.

The tested products were administered, orally in the form of a 3% aqueous solution of tragacanth gum in the ratio of 1 ml per 100 g of body weight, in an amount corresponding to 250 mg/kg.

To carry out these tests, a hyperlipidemia was caused in the animals, by means of the product marketed by the ROHM and HAAS Company under the name TRITON W.R.

In fasting rats, the intravenous injection of TRITON resulted in a particularly distinct hyperlipidemia as regards triglycerides and to a lesser extent as regards total lipids.

On this hyperlipidemia the effects obtained by the administration of the active substances according to the invention, are observed.

The tests were carried out as follows:

the rats were fasted for 18 hours, then the TRITON W.R. was administered intravenously in 10% aqueous solution in the proportion of 200 mg/kg;

simultaneously 250 mg/kg of the product under test was administered orally;

6 hours and/or 24 hours later, blood assays were carried out conventionally.

The results of these tests are shown in Table VII of the following page.

The results are expressed in percentage of decrease caused by the product under test with respect to the TRITON control which had resulted in a hyperlipidemia are shown, this percentage decrease being respectively relative:

to the total cholesterol,
to the total lipids,
to the triglycerides.

Among the products tested, the products having remarkable pharmacological properties with respect to lipid regulating are those belonging to the above defined groups, as follows:

$B_1$, $E_1$, $E_2$, $G_1$, $G_2$, $H_1$, $H_2$, K, L, M, N, $S_1$, $S_2$ T, Y, Z.

TABLE VII

| | LIPID REGULATING ACTIVITY | | |
|---|---|---|---|
| | % of decrease with respect to Triton control | | |
| | Total cholesterol | Total lipids | Triglycerides |
| 362 | −10 | −39 | −88 |
| 380 | −19 | −31 | −86 |
| 387 | (*) | −39 | −90 |
| 469 | −3 | −30 | −28 |
| 472 | | −9 | |
| 484 | | −41 | |
| 486 | | −66 | −21 |
| 501 | −24 | −17 | −18 |
| 502 | −16 | −45 | −32 |
| 503 | | −26 | −18 |
| 504 | −45 | | |
| 505 | | −48 | −17 |
| 508 | −8 | −17 | |
| 562 | | −6 | |

TABLE VII-continued

LIPID REGULATING ACTIVITY
% of decrease with respect to Triton control

| | Total cholesterol | Total lipids | Triglycerides |
|---|---|---|---|
| 563 | −8 | −27 | |
| 564 | | −37 | −15 |
| 608 | −19 | −15 | |
| 609 | −40 | | −2 |
| 610 | −20 | −2 | |
| 611 | −29 | −15 | |
| 612 | −1 | −48 | −13 |
| 624 | −18 | | |
| 625 | | | −5 |
| 626 | −18 | | |
| 656 | −14 | −3 | −29 |
| 660 | −42 | −36 | −90 |
| 661 | −37 | | −86 |
| 665 | −15 | −30 | −20 |
| 666 | | −20 | |
| 667 | −7 | −45 | |
| 668 | −27 | −20 | −29 |
| 675 | −19 | −45 | −27 |
| 676 | −10 | −43 | −24 |
| 679 | −30 | −61 | −34 |
| 680 | | −46 | −16 |
| 681 | −32 | −51 | −33 |
| 682 | | −22 | −34 |
| 683 | | −19 | −52 |
| 693 | −31 | −18 | −45 |
| 694 | −32 | −31 | −65 |
| 695 | −24 | −20 | −27 |
| 696 | −56 | −46 | −59 |
| 697 | −46 | −35 | −50 |
| 728 | | −32 | −53 |
| 729 | | | −17 |
| 730 | | | −10 |
| 786 | −36 | −24 | −17 |
| 800 | −13 | −33 | −5 |
| 823 | −41 | −25 | |

(*)The absence of values means that the effect is nul or that the control group has not reacted normally with respect to Triton administration.

TABLE VIII
PREFERRED MEDICAMENTS

| Compound no | Normolip. | compound no | Normolip. |
|---|---|---|---|
| 362 | + | 679 | +++ |
| 380 | + | 680 | + |
| 387 | + | 681 | +++ |
| 503 | | 682 | + |
| 563 | + | 683 | + |
| 612 | | 693 | + |
| 660 | +++ | 694 | ++ |
| 661 | + | 696 | ++++ |
| 667 | + | 697 | ++ |
| 668 | ++++ | 728 | ++ |
| 675 | +++ | 786 | + |
| 676 | | | |

2. Atherosclerosis inducing diet

In a second experimental series, tha activity of certain products according to the invention were tested on animals which had received an atherosclerosis inducing diet for a long period.

The test was carried out on Wistar female rats, of weight about 160–180 g.

The animals received food coming from the National Nutrition plant of Villemoisson-sur-Orge, France, and denoted by the reference UAR A03, enriched in cholesterol (0.5%) and in cholic acid (0.5%).

After 15 days of the atherosclerosis inducing diet and whilst maintaining the animals on an atherosclerosis inducing diet, they were given orally for 4 days 250.000 iu/kg of vitamine $D_2$ marketed under the name Sterogyl 25H, in solution in olive oil.

Then the products under study were administered for 4 weeks, from the end of the administration of the lesion-inducing agent.

At the end of the study, biochemical examinations were carried out on all the animals [total cholesterol, high density lipoprotein (HDL) and cholesterol low density lipoprotein (LDL), and triglycerides].

Autopsy and histological study

At the end of the study, all the animals still alive were sacrificed, and various organs were removed, particularly the aorta, for histological study of the latter. Two criteria were examined: the number of atherosclerosis areas and the severity of the lesions.

Calculation of the figures was carried out in the following manner:

- as regards the severity of the lesions, a quotation ranging from 0 for absence of a lesion to 5+ for the severest lesions was made, and this for each type of alteration concerned (increase of interlamellar spaces, interruption of elastic laminae, thickening of the elastic laminae, calcium deposition, mucopolysaccharide deposition); then all of the results per batch of animals were added;
- as regards the number of atherosclerosis areas, by counting the latter and adding all the figures obtained per batch of animals.

Then the percentage reduction with respect to the diet controls and the score were calculated, that is to say the ratio of the intensity of the activity of the product tested with respect to that of the activity of clofibrate, reckoned as 1.

Table IX gives the detailed results of the biochemical examination:

(a) in % reduction with respect to the control diet;
(b) as score, with respect to the reference product, clofibrate, the latter being counted as 1.

Table X gives the results of macroscopic examinations:

(a) in % decrease in animals afflicted with lesions;
(b) as score with respect to the reference clofibrate, of which the score was counted as 1.

Table XI gives the microscopic results with histological quotation as regards the severity of the lesions, and the number of atherosclerotic areas.

TABLE IX

| | BIOCHEMICAL EXAMS | | | | | | | |
|---|---|---|---|---|---|---|---|---|
| | CHOLESTEROL T | | CHOLESTEROL HDL | | CHOLESTEROL LDL | | TRIGLYCERIDES | |
| Batch | % | Score | % | Score | % | Score | % | Score |
| TEM diet | | | | | | | | |
| CLOFIBRATE | −48,75 | 1,00 | +104,17 | 1,00 | −55,37 | 1,00 | −24,14 | 1,00 |
| 679 | −53,13 | 1,09 | +58,33 | 0,56 | −60,14 | 1,09 | 0 | 0 |
| 786 | −54,22 | 1,11 | −20,83 | — | −57,07 | 1,03 | −17,24 | 0,71 |
| 1038 | −51,88 | 1,06 | +83,33 | 0,80 | −58,26 | 1,05 | −20,69 | 0,86 |

TABLE X

MACROSCOPIC EXAMS

| BATCH | % | AFFECTED ANIMALS % of decrease TEM-diet | SCORE CLOFIBRATE |
|---|---|---|---|
| TEM-TEM | 0 | — | — |
| TEM-diet | 100 | — | — |
| CLOFIBRATE | 81,82 | 18,18 | 1,00 |
| 679 | 92,86 | 7,14 | 0,39 |
| 786 | 93,33 | 6,67 | 0,37 |
| 1038 | 66,67 | 33,33 | 1,83 |

TABLE XI

MICROSCOPIC OBSERVATIONS

| Batch | HISTOLOGICAL QUOTATION % | % of decrease TEM-diet | SCORE CLOFIBRATE | NUMBER OF ATHEROSCLEROTIC AREAS % | % of decrease TEM-diet | SCORE CLOFIBRATE |
|---|---|---|---|---|---|---|
| TEM-TEM | — | — | — | — | — | — |
| TEM-diet | 132 | — | — | 160 | — | — |
| CLOFIBRATE | 49 | 62, 83 | 1, 00 | 72 | 54, 93 | 1, 00 |
| 679 | 79 | 39, 97 | 0, 64 | 82 | 48, 57 | 0, 88 |
| 786(*) | | | | | | |
| 1038 | 44 | 66, 31 | 1, 06 | 35 | 78, 18 | 1, 42 |

(*)non examined with respect to histological point of view

TOXICITY

The acute toxicity is expressed by the lethal dose 50, that is to say the dose resulting in the death of 50% of the animals.

This study was carried out on mice, to which the products under test were administered intraperitoneally.

The test carried out showed that the lethal dose 50 of the active substances was very high. It was established as follows, for the following substances:

| | |
|---|---|
| 362 | lethal dose 50 (mg/kg) is = 1,760 |
| 387 | lethal dose 50 (mg/kg) is = 3,070 |
| 502 | lethal dose 50 (mg/kg) is = 3,070 |
| 665 | lethal dose 50 (mg/kg) is > 6,400 |
| 675 | lethal dose 50 (mg/kg) is = 930 |
| 676 | lethal dose 50 (mg/kg) is > 6,400 |
| 729 | lethal dose 50 (mg/kg) is > 6,400 |

For compound no. 1 038, the study of the toxicity has been carried out on rats and on mice to which the product has been administered by the oral route.

The results (expressed in g/kg) relative to $LD_{50}$, $LD_0$, and $LD_{100}$ are gathered in the following table.

| | Male | Female |
|---|---|---|
| Rats | | |
| $LD_{50}$ | 13 | 15.5 |
| $LD_0$ | 5 | 5 |
| $LD_{100}$ | 20 | >20 |
| Mice | | |
| $LD_{50}$ | 6 | 6.6 |
| $LD_0$ | 4 | 5 |
| $LD_{100}$ | 9 | 9 |

It results that compound no. 1 038 presents no toxicity.

The medicaments according to the invention are advantageously used as active principle in the treatment of certain disorders of lipid metabolism.

The medicaments according to the invention are devoid of toxicity.

The ratio active dose/toxic dose can be compared favorably with that of known substances having properties of the same nature.

By way of example, the tests of subacute toxicity carried out on the compound no. 1 038, for about one month, at the rate of 150,500 and 1 000 mg/kg show that the therapeutic index of this compound is very satisfactory.

Besides the active substances constituted by the compounds of formula (I), the medicaments according to the invention may contain other active substances compatible with the first ones. For instance, the compounds which are part of the medicaments according to the invention, can be associated with lipid regulating agents of the biguanide type such as 1,1-dimethylbiguanide or 1-butylbiguanide or with lipid regulating agents which are derived from nicotinic acid.

In these medicaments according to the invention, the active substances are associated, to the extent that this is necessary, with traditional excipients and adjuvants to facilitate and improve their use, their preservation, etc.

In particular, the active substances are associated with solid or liquid excipients facilitating their administration according to the route of introduction.

Taking into account their activities and the treatments for which they are used, the medicaments according to the invention may be administered parenterally, preferably when the active substance is in the form of salt. For this purpose, they are presented in the form of sterile or sterilizable solutions, injectable or suitable for use, for the extemporaneous preparation of injectable solutions. These solutions may be presented in the form of physiological aqueous solutions, particularly isotonic solutions of one of these compounds such as saline or glucose isotonic solutions, the examples not having, of course, any limiting nature in the definition of the physiologically acceptable products which can be used to form injectable isotonic solutions.

The medicaments according to the invention may also be administered by other routes, particularly suppositories or orally. Administered orally, they are presented in very varied form: tablets, losenges, capsules, gelatine capsules, powders, solutions, suspensions, syrups, or topically as a cream, pommade, lotion, gel, etc.

In pharmaceutical presentations for administration in the parenteral route, the dose of product to be administered, per kilogram weight of patient, is comprised from about 0.5 to about 25 mg.

By the oral route, the unit dose is comprised from about 10 mg to about 500 mg, preferably from 50 mg to 250 mg.

By the topical route, the presentations include from 1 to 20% of the preparation.

We claim:

1. An orally administrable pharmaceutical unit dose form selected from the group consisting of a tablet, a capsule, and a lozenge, comprising an effective blood lipid level lowering amount from 10 to 500 milligrams of a compound of the formula:

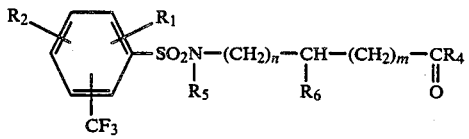

wherein $R_1$ and $R_2$ are each hydrogen, halogen, $-NO_2$, $-NH_2$, $-CF_3$, alkyl having from 1 to 6 carbon atoms or alkoxy having from 1 to 6 carbon atoms;

$n+m+1$ is from 3 to 11, $R_5$ and $R_6$ are each hydrogen, alkyl having 1 to 6 carbon atoms or aralkyl having from 7 to 9 carbon atoms, and $R_4$ is hydroxy or $OR_7$ in which $R_7$ is alkyl having from 1 to 6 carbon atoms;

or a pharmaceutically acceptable salt thereof and a sterile pharmaceutical carrier.

2. An orally administrable pharmaceutical unit dose form according to claim 1, comprising from 50 to 250 milligrams of said compound or pharmaceutically acceptable salt thereof.

3. An orally administrable pharmaceutical unit dose form according to claim 1, wherein $R_5$ is hydrogen or methyl and $R_6$ is hydrogen.

4. An orally administrable pharmaceutical unit dose form according to claim 3, wherein $R_1$ and $R_2$ are each hydrogen and $n+m+1$ is 3, 5 or 10.

5. An orally administrable pharmaceutical unit dose form according to claim 4, wherein $n+m+1$ is 3 and $R_4$ is hydroxy.

* * * * *